United States Patent
Harrison et al.

(10) Patent No.: US 6,211,352 B1
(45) Date of Patent: Apr. 3, 2001

(54) METHOD FOR THE DIAGNOSIS AND TREATMENT OF GLUTAMIC ACID DECARBOXYLASE AUTOANTIGEN ASSOCIATED DISEASES

(75) Inventors: Leonard Harrison; Margot Honeyman, both of St. Kilda West; David Cram, Blackburn South; Henry De Aizpurua, Blackburn, all of (AU)

(73) Assignee: Amrad Corporation Limited, Richmond (AU)

( * ) Notice: Subject to any disclaimer, the term of this patent is extended or adjusted under 35 U.S.C. 154(b) by 0 days.

(21) Appl. No.: 09/124,141

(22) Filed: Jul. 29, 1998

Related U.S. Application Data

(63) Continuation of application No. 08/308,952, filed on Sep. 20, 1994, now Pat. No. 5,837,812, which is a continuation of application No. 07/839,805, filed on Feb. 21, 1992, now abandoned.

(30) Foreign Application Priority Data

Feb. 22, 1991 (AU) .............................................. PK-4773/91
Sep. 27, 1991 (AU) .............................................. PK-8620/91

(51) Int. Cl.$^7$ ......................... C07H 21/02; C07H 21/04; C12N 15/00
(52) U.S. Cl. ...................... 536/23.2; 536/23.1; 536/24.1; 536/24.2; 435/320.1
(58) Field of Search ................................ 536/23.2, 23.4, 536/23.1, 24.1, 24.2; 435/320.1

(56) References Cited

U.S. PATENT DOCUMENTS 5,705,626 * 1/1998 Tobin et al. ......................... 536/23.5

FOREIGN PATENT DOCUMENTS

WO 92/04632 9/1991 (WO) .
WO 92/03733 3/1992 (WO) .
WO 92/05446 4/1992 (WO) .

OTHER PUBLICATIONS

Sambrook et al., Molecular Cloning, A Laboratory Manual, Second Edition, 1989, Cold Spring Harbor Laboratory, Cold Spring Harbor, NY, pp. 16.3–16.4.*

Baekkeskov, et al. (Mar. 1987) "Antibodies to a 64,000 $M_r$ Human Islet Cell Antigen Precede the Clinical Onset of Insulin–Dependent Diabetes", *J. Clin. Invest.* 79 :926–934.

Baekkeskov, et al. (Sep. 13, 1990) "Identification of the 64K Autoantigen in Insulin–Dependent Diabetes as the GABA–Synthesizing Enzyme Glutamic Acid Decarboxylase", *Nature* 347:151–156.

Bond, et al. (May 1988) "Pattern of Expression of Glutamic Acid Decarboxylase mRNA in the Developing Rat Brain", *Proc. Natl. Acad. Sci. USA* 85:3231–3234.

Chang, et al. (Jun. 1988) "Characterization of the Proteins Purified with Monoclonal Antibodies in Glutamic Acid Decarboxylase", *The Journal of Neuroscience* 8(6):2123–2130.

Erlander, et al. (Jul. 1991) "Two Genes Encode Distinct Glutamate Decarboxylases", *Neuron* 7:91–100.

Jackson, et al. (1990) "Drosophila GABAergic Systems: Sequence and Expression of Glutamic Acid Decarboxylase", *Journal of Neurochemistry* 54(3) : 1068–1078.

Julien, et al. (1987) "Molecular Cloning, Expression and in situ Hybridization of Rat Brain Glutamic Acid Decarboxylase Messenger RNA", *Neuroscience Letters* 73:173–180.

Julien, et al. (1990) "Rat Brain Glutamic Acid Decarboxylase Sequence Deduced from a Cloned cDNA", *Journal of Neurochemistry* 54(2) : 703–705.

Katarova, et al. (1990) "Molecular Identification of the 62 kd Form of Glutamic Acid Decarboxylase from the Mouse", *European Journal of Neuroscience* 2(3) : 190–202.

Kaufman, et al. (May 1986) "Brain Glutamate Decarboxylase Cloned in λ–11: Fusion Protein Produces γ–Aminobutyric Acid", *Science* 232:1138–1140.

Kaufman, et al. (Jan. 1992) "Autoimmunity to Two forms of Glutamate Decarboxylase in Insulin–Dependent Diabetes Mellitus", *J. Clin. Invest.* 89:283–292.

Persson, et al. (Sep. 1990) "Expression of Neurotransmitter–Synthesizing Enzyme Glutamic Acid Decarboxylase in Male Germ Cells", *Molecular and Cellular Biology* 10(9) : 4701–4711.

Solimena, et al. (May 31, 990) "Autoantibodies to GABA–ergic Neurons and Pancreatic Beta Cells in Stiff–Man Syndrome", *The New England Journal of Medicine* 322(22) : 1555–1572.

Wyborski, et al. (1990) "Characterization of a cDNA Coding for Rat Glutamic Acid Decarboxylase", *Molecular Brain Research* 8:193–198.

* cited by examiner

*Primary Examiner*—Christina Y. Chan
*Assistant Examiner*—Karen Clemens
(74) *Attorney, Agent, or Firm*—Scully, Scott, Murphy & Presser

(57) ABSTRACT

The present invention relates to the identification, cloning and sequencing of nucleic acid molecules encoding an isoform of the enzyme glutamic acid decarboxylase and further relates to the use of these molecules and/or peptides and polypeptides encoded thereby in diagnostic tests for Insulin Dependent Diabetes Mellitus and other diseases in which glutamic acid decarboxylase is an autoantigen and in the treatment of patients suffering from these diseases.

11 Claims, 15 Drawing Sheets

|         | 10         | 20         | 30         | 40         | 50    |
|---------|------------|------------|------------|------------|-------|
| HBGAD   | ATTGCACCCGTGTTTGTTCTCATGGAACAGATTACTCTTAAGAAGATGAG |
| HIGAD   | ATTGCACCCGTGTTTGTTCTCATGGAACAGATTACTCTTAAGAAGATGAG |

|         | 60         | 70         | 80         | 90         | 100   |
|---------|------------|------------|------------|------------|-------|
| HBGAD   | AAAGATCGTTGGATGGTCAAATAAAGATGGTGATGGGTTATTTTCTCCTG |
| HIGAD   | AAAGATCGTTGGATGGTCAAATAAAGATGGTGATGGGTTACTTTCTCCTG |

|         | 110        | 120        | 130        | 140        | 150   |
|---------|------------|------------|------------|------------|-------|
| HBGAD   | GGGGAGCCATATCCAATATGTACAGCACCATGGCTGCTCGTTACAAGTAC |
| HIGAD   | GGGGAGCCATATCCAATATGTACAGCATCATGGCTGCTCGTTACAAGTAC |

|         | 160        | 170        | 180        | 190        | 200   |
|---------|------------|------------|------------|------------|-------|
| HBGAD   | TTCCCAGAAGTGAAGACAAAAGGCATGGCGGCTGTGCCCAAACTGGTCCT |
| HIGAD   | TTCCCAGAAGTGAAGACAAAAGGCATGGCGGCTGTGCCCAAACTGGTCCT |

|         | 210        | 220        | 230        | 240        | 250   |
|---------|------------|------------|------------|------------|-------|
| HBGAD   | CTTCACCTCAGAACACAGTCACTATTCCATAAAGAAAGCCGGGGCTGCGC |
| HIGAD   | CTTCACCTCAGAACACAGTCACTATTCCATAAAGAAAGCCGGGGCTGCGC |

|         | 260        | 270        | 280        | 290        | 300   |
|---------|------------|------------|------------|------------|-------|
| HBGAD   | TTGGCTTTGGAACCGACAATGTGATTTTGATAAAGTGCAATGAAAGGGGG |
| HIGAD   | TTGGCTTTGGAACCGACAATGTGATTTTGATAAAGTGCAATGAAAGGGGG |

|         | 310        | 320        | 330        | 340        | 350   |
|---------|------------|------------|------------|------------|-------|
| HBGAD   | AAGATAATTCCGGCTGATTTAGAGGCAAAAATTCTTGATGCCAAACAAAA |
| HIGAD   | AAGATAATTCCGGCTGATTTAGAGGCAAAAATTCTTGATGCCAAACAAAA |

FIG.IA

```
                360        370        380        390        400
HBGAD    GGGCTATGTTCCCCTCTATGTCAATGCAACCGCAGGCACGACTGTTTACG

HIGAD    GGGCTATGTTCCCCTTTATGTCAATGCAACCGCAGGCACGACTGTTTACG 410        420        430        440        450
HBGAD    CAGCATTCGATCCAATCCAGGAAATTGCGGACATATGTGAGAAATACAAC

HIGAD    GAGCATTCGATCCAATCCAGGAAATTGCGGACATATGTGAGAAATACAAC 460        470        480        490        500
HBGAD    CTTTGGCTGCATGTGGATGCTGCCTGGGGTGGTGGACTGCTCATGTCCCG

HIGAD    CTTTGGCTGCATGTGGATGCTGCCTGGGGTGGTGGACTGCTCATGTCCCG 510        520        530        540        550
HBGAD    GAAGCACCGCCACAAACTCAGCGGCATAGAAAGGGCCAATTCA

HIGAD    GAAGCACCGCCACAAACTCAGCGGCATAGAAAGGGCCAATTCA
```

FIG.1B

```
                                     **              *
HBGAD    IAPVFVLMEQITLKKMRKIVGWSNKDGDGLFSPGGAISNMYSTMAARYKY

HIGAD    IAPVFVLMEQITLKKMRKIVGWSNKDGDGILSPGGAISNMYSIMAARYKY

FBGAD    IAPVFVLMEQITLKKMREIVGWSSKDGDGIFSPGGAISNMYSIMAARYKF

HBGAD    FPEVKTKGMAAVPKLVLFTSEHSHYSIKKAGAALGFGTDNVILIKCNERG

HIGAD    FPEVKTKGMAAVPKLVLFTSEHSHYSIKKAGAALGFGTDNVILIKCNERG

FBGAD    FPEVKTKGMAAVPKLVLFTSEHSHYSIKKAGAALGFGTDNVILIKCNERG

HBGAD    KIIPADLEAKILDAKQKGYVPLYVNATAGTTVYGAFDPIQEIADICEKYN

HIGAD    KIIPADLEAKILDAKQKGYVPLYVNATAGTTVYGAFDPIQEIADICEKYN

FBGAD    KIIPADLEAKILEAKQKGYVPLYVNATAGTTVYGAFDPIQEIADICEKYN

HBGAD    LWLHVDAAWGGGLLMSRKHRHKLSGIERANS

HIGAD    LWLHVDAAWGGGLLMSRKHRHKLSGIERANS

FBGAD    LWLHVDAAWGGGLLMSRKHRHKLSGIERANS
```

*aa differences between HBGAD and HIGAD

FIG. 2

```
  M  A  S  S  T  P  S  P  A  T  S  S  N  A  G  A  D  P  N  T
ATGGCGTCTTCCACTCCTTCGCCTGCAACCTCCTCGAACGCGGGAGCGGATCCTAATACT    60

T  N  L  R  P  T  T  Y  D  T  W  C  G  V  A  H  G  C  T  R
ACCAACCTGCGCCCTACAACGTATGATACTTGGTGTGGCGTAGCCCATGGATGCACCAGA   120

K  L  G  L  K  I  C  G  F  L  Q  R  T  N  S  L  E  E  K  S
AAACTGGGCCTGAAGATCTGTGGCTTCTTACAAAGGACCAATAGCCTGGAAGAGAAGAGT   180

R  L  V  S  A  F  R  E  R  Q  S  S  K  N  L  L  S  C  E  N
CGTCTTGTGAGCGCCTTCAGGGAGAGGCAGTCCTCCAAGAACCTGCTTTCCTGTGAAAAC   240

S  D  Q  G  A  R  F  R  R  T  E  T  D  F  S  N  L  F  A  Q
AGTGACCAGGGTGCCCGCTTCCGGCGCACAGAGACCGACTTCTCCAACCTGTTTGCTCAA   300

D  L  L  P  A  K  N  G  E  E  Q  T  A  Q  F  L  L  E  V  V
GATCTGCTTCCAGCTAAGAACGGGGAGGAGCAAACTGCGCAGTTCTTGCTGGAAGTGGTA   360

D  I  L  L  N  Y  V  R  K  T  F  D  R  S  T  K  V  L  D  F
GACATACTCCTCAACTATGTCCGCAAGACATTTGATCGCTCCACCAAGGTTCTGGATTTC   420

H  H  P  H  Q  L  L  E  G  M  E  G  F  N  L  E  L  S  D  H
CACCACCCACACCAGTTGCTGGAAGGCATGGAAGGCTTTAATTTGGAGCTGTCTGACCAC   480

P  E  S  L  E  Q  I  L  V  D  C  R  D  T  L  K  Y  G  V  R
CCCGAGTCTCTGGAGCAGATCCTGGTTGACTGTAGAGACACCCTGAAGTACGGGGTTCGC   540

T  G  H  P  R  F  F  N  Q  L  S  T  G  L  D  I  I  G  L  A
ACAGGTCACCCTCGATTTTTCAACCAGCTCTCTACTGGTTTGGATATCATTGGTTTAGCT   600

G  E  W  L  T  S  T  A  N  T  N  M  F  T  Y  E  I  A  P  V
GGCGAATGGCTGACATCGACTGCCAATACCAATATGTTCACATATGAAATTGCACCCGTG   660

F  V  L  M  E  Q  I  T  L  K  K  M  R  K  I  V  G  W  S  N
TTTGTTCTCATGGAACAGATTACTCTTAAGAAGATGAGAAAGATCGTTGGATGGTCAAAT   720

K  D  G  D  G  I  F  S  P  G  G  A  I  S  N  M  Y  S  I  M
AAAGATGGTGATGGGATATTTTCTCCTGGGGGAGCCATATCCAATATGTACAGCATCATG   780

A  A  R  Y  K  Y  F  P  E  V  K  T  K  G  M  A  A  V  P  K
GCTGCTCGTTACAAGTACTTCCCAGAAGTGAAGACAAAAGGCATGGCGGCTGTGCCCAAA   840

L  V  L  F  T  S  E  H  S  H  Y  S  I  K  K  A  G  A  A  L
CTGGTCCTCTTCACCTCAGAACACAGTCACTATTCCATAAAGAAAGCCGGGGCTGCGCTT   900

G  F  G  T  D  N  V  I  L  I  K  C  N  E  R  G  K  I  I  P
GGCTTTGGAACCGACAATGTGATTTTGATAAAGTGCAATGAAAGGGGGAAGATAATTCCG   960

A  D  L  E  A  K  I  L  D  A  K  Q  K  G  Y  V  P  L  Y  V
GCTGATTTAGAGGCAAAAATTCTTGATGCCAAACAAAAGGGCTATGTTCCCCTTTATGTC  1020
```

FIG.3A

```
         N  A  T  A  G  T  T  V  Y  G  A  F  D  P  I  Q  E  I  A  D
      AATGCAACCGCAGGCACGACTGTTTACGGAGCATTCGATCCAATCCAGGAAATTGCGGAC 1080

I  C  E  K  Y  N  L  W  L  H  V  D  A  A  W  G  G  G  L  L
      ATATGTGAGAAATACAACCTTTGGCTGCATGTGGATGCTGCCTGGGGTGGTGGACTGCTC 1140

M  S  R  K  H  R  H  K  L  S  G  I  E  R  A  N  S  V  T  W
      ATGTCCCGGAAGCACCGCCACAAACTCAGCGGCATAGAAAGGGCCAATTCAGTCACCTGG 1200

N  P  H  K  M  M  G  V  L  L  Q  C  S  A  I  L  V  K  E  K
      AACCCTCACAAGATGATGGGCGTGCTGCTCCAGTGCTCTGCCATTCTGGTCAAGGAAAAG 1260

G  I  L  Q  G  C  N  Q  M  C  A  G  Y  L  F  Q  P  D  K  Q
      GGTATACTCCAAGGATGCAACCAGATGTGTGCAGGCTACCTCTTCCAGCCAGACAAGCAG 1320

Y  D  V  S  Y  D  T  G  D  K  A  I  Q  C  G  R  H  V  D  I
      TATGACGTCTCCTATGACACCGGGGACAAGGCGATTCAGTGTGGCCGCCATGTGGACATC 1380

F  K  F  W  L  M  W  K  A  K  G  T  V  G  F  E  N  Q  I  N
      TTCAAGTTCTGGCTGATGTGGAAAGCAAAGGGCACCGTGGGATTTGAAAACCAGATCAAC 1440

K  C  L  E  L  A  D  Y  L  Y  A  K  I  K  N  R  E  E  P  E
      AAATGCCTGGAGCTGGCTGATTACCTCTACGCCAAGATTAAAAACAGAGAAGAGTTTGAG 1500

M  V  F  D  G  E  P  E  H  T  N  V  C  F  W  Y  I  P  Q  S
      ATGGTTTTCGATGGTGAGCCTGAGCACACAAATGTCTGTTTCTGGTACATTCCACAAAGC 1560

L  R  G  V  P  D  S  P  E  R  R  E  K  L  H  R  V  A  P  K
      CTTAGAGGGGTTCCAGATAGCCCTGAGCGACGAGAAAAGCTACACAGGGTGGCTCCCAAG 1620

I  K  A  L  M  M  E  S  G  T  T  M  V  G  Y  Q  P  Q  G  D
      ATCAAAGCTCTGATGATGGAGTCAGGAACAACCATGGTCGGCTACCAGCCTCAAGGGGAC 1680

K  A  N  F  F  R  N  V  I  S  N  P  A  A  T  Q  S  D  I  D
      AAGGCCAACTTCTTCCGGATGGTCATCTCTAACCCAGCCGCCACCCAGTCTGACATCGAT 1740

F  L  I  E  E  I  E  R  L  G  Q  D  L  *
      TTCCTCATTGAGGAGATAGAGAGGTTGGGCCAGGATCTGTAA                    1782
```

FIG.3B

```
  M   A   S   S   T   P   S   P   A   T   S   S   N   A   G   A   D   P   N   T
ATGGCGTCTTCCACTCCTTCGCCTGCAACCTCCTCGAACGCGGGAGCGGATCCTAATACT    60

T   N   L   R   P   T   T   Y   D   T   W   C   G   V   A   H   G   C   T   R
ACCAACCTGCGCCCTACAACGTATGATACTTGGTGTGGCGTAGCCCATGGATGCACCAGA   120

K   L   G   L   K   I   C   G   F   L   Q   R   T   N   S   L   E   E   K   S
AAACTGGGCCTGAAGATCTGTGGCTTCTTACAAAGGACCAATAGCCTGGAAGAGAAGAGT   180

R   L   V   S   A   F   R   E   R   Q   S   S   K   N   L   L   S   C   E   N
CGTCTTGTGAGCGCCTTCAGGGAGAGGCAGTCCTCCAAGAACCTGCTTTCCTGTGAAAAC   240

S   D   Q   G   A   R   F   R   R   T   E   T   D   F   S   N   L   F   A   Q
AGTGACCAGGGTGCCCGCTTCCGGCGCACAGAGACCGACTTCTCCAACCTGTTTGCTCAA   300

D   L   L   P   A   K   N   G   E   E   Q   T   A   Q   F   L   L   E   V   V
GATCTGCTTCCAGCTAAGAACGGGGAGGAGCAAACTGCGCAGTTCTTGCTGGAAGTGGTA   360

D   I   L   L   N   Y   V   R   K   T   F   D   R   S   T   K   V   L   D   F
GACATACTCCTCAACTATGTCCGCAAGACATTTGATCGCTCCACCAAGGTTCTGGATTTC   420

H   H   P   H   Q   L   L   E   G   M   E   G   F   N   L   E   L   S   D   H
CACCACCCACACCAGTTGCTGGAAGGCATGGAAGGCTTTAATTTGGAGCTGTCTGACCAC   480

P   E   S   L   E   Q   I   L   V   D   C   R   D   T   L   K   Y   G   V   R
CCCGAGTCTCTGGAGCAGATCCTGGTTGACTGTAGAGACACCCTGAAGTACGGGGTTCGC   540

T   G   H   P   R   F   F   N   Q   L   S   T   G   L   D   I   I   G   L   A
ACAGGTCACCCTCGATTTTTCAACCAGCTCTCTACTGGTTTGGATATCATTGGTTTAGCT   600

G   E   W
GGCGAATGG                                                      609
```

FIG.4

```
  G  L  A  G  E  W  L  T  S  T  A  N  T  N  M  F  T  Y  E  I
GGTTTAGCTGGCGAATGGCTGACATCGACTGCCAATACCAATATGTTCACATATGAAATT  651

A  P  V  F  V  L  M  E  Q  I  T  L  K  K  M  R  K  I  V  G
GCACCCGTGTTTGTTCTCATGGAACAGATTACTCTTAAGAAGATGAGAAAGATCGTTGGA  711

W  S  N  K  D  G  D  G  I  F  S  P  G  G  A  I  S  N  M  Y
TGGTCAAATAAAGATGGTGATGGGATATTTTCTCCTGGGGGAGCCATATCCAATATGTAC  771

S  I  M  A  A  R  Y  K  Y  F  P  E  V  K  T  K  G  M  A  A
AGCATCATGGCTGCTCGTTACAAGTACTTCCCAGAAGTGAAGACAAAAGGCATGGCGGCT  831

V  P  K  L  V  L  F  T  S  E  H  S  H  Y  S  I  K  K  A  G
GTGCCCAAACTGGTCCTCTTCACCTCAGAACACAGTCACTATTCCATAAAGAAAGCCGGG  891

A  A  L  G  F  G  T  D  N  V  I  L  I  K  C  N  E  R  G  K
GCTGCGCTTGGCTTTGGAACCGACAATGTGATTTTGATAAAGTGCAATGAAAGGGGGAAG  951

I  I  P  A  D  L  E  A  K  I  L  D  A  K  Q  K  G  Y  V  P
ATAATTCCGGCTGATTTAGAGGCAAAAATTCTTGATGCCAAACAAAAGGGCTATGTTCCC 1011

L  Y  V  N  A  T  A  G  T  T  V  Y  G  A  F  D  P  I  Q  E
CTTTATGTCAATGCAACCGCAGGCACGACTGTTTACGGAGCATTCGATCCAATCCAGGAA 1071

I  A  D  I  C  E  K  Y  N  L  W  L  H  V  D  A  A  W  G  G
ATTGCGGACATATGTGAGAAATACAACCTTTGGCTGCATGTGGATGCTGCCTGGGGTGGT 1131

G  L  L  M  S  R  K  H  R  H  K  L  S  G  I  E  R  A  N  S
GGACTGCTCATGTCCCGGAAGCACCGCCACAAACTCAGCGGCATAGAAAGGGCCAATTCA 1191

V  T  W  N  P  H
GTCACCTGGAACCCTCAC                                           1209
```

FIG.5

```
          G  I  E  R  A  N  S  V  T  W  N  P  H  K  M  M  G  V  L  L
         GGCATAGAAAGGGCCAATTCAGTCACCTGGAACCCTCACAAGATGATGGGCGTGCTGCTC  1230

Q  C  S  A  I  L  V  K  E  K  G  I  L  Q  G  C  N  Q  M  C
         CAGTGCTCTGCCATTCTGGTCAAGGAAAAGGGTATACTCCAAGGATGCAACCAGATGTGT  1290

A  G  Y  L  F  Q  P  D  K  Q  Y  D  V  S  Y  D  T  G  D  K
         GCAGGCTACCTCTTCCAGCCAGACAAGCAGTATGACGTCTCCTATGACACCGGGGACAAG  1350

A  I  Q  C  G  R  H  V  D  I  F  K  F  W  L  M  W  K  A  K
         GCGATTCAGTGTGGCCGCCATGTGGACATCTTCAAGTTCTGGCTGATGTGGAAAGCAAAG  1410

G  T  V  G  F  E  N  Q  I  N  K  C  L  E  L  A  D  Y  L  Y
         GGCACCGTGGGATTTGAAAACCAGATCAACAAATGCCTGGAGCTGGCTGATTACCTCTAC  1470

A  K  I  K  N  R  E  E  F  E  M  V  F  D  G  E  P  E  H  T
         GCCAAGATTAAAAACAGAGAAGAGTTTGAGATGGTTTTCGATGGTGAGCCTGAGCACACA  1530

N  V  C  F  W  Y  I  P  Q  S  L  R  G  V  P  D  S  P  E  R
         AATGTCTGTTTCTGGTACATTCCACAAAGCCTTAGAGGGGTTCCAGATAGCCCTGAGCGA  1590

R  E  K  L  H  R  V  A  P  K  I  K  A  L  M  M  E  S  G  T
         CGAGAAAAGCTACACAGGGTGGCTCCCAAGATCAAAGCTCTGATGATGGAGTCAGGAACA  1650

T  M  V  G  Y  Q  P  Q  G  D  K  A  N  F  F  R  M  V  I  S
         ACCATGGTCGGCTACCAGCCTCAAGGGGACAAGGCCAACTTCTTCCGGATGGTCATCTCT  1710

N  P  A  A  T  Q  S  D  I  D  F  L  I  E  E  I  E  R  L  G
         AACCCAGCCGCCACCCAGTCTGACATCGATTTCCTCATTGAGGAGATAGAGAGGTTGGGC  1770

Q  D  L  *
         CAGGATCTGTAA                                                  1782
```

FIG. 6

```
  M  A  S  S  T  P  S  S  S  A  T  S  S  N  A  G  A  D  P  N
ATGGCGTCTTCGACCCCATCTTCGTCCGCAACCTCCTCGAACGCGGGAGCGGACCCCAAT   60

T  T  N  L  R  P  T  T  Y  D  T  W  C  G  V  A  H  G  C  T
ACCACTAACCTGCGCCCCACAACGTACGATACCTGGTGCGGCGTGGCCCATGGATGCACC  120

R  K  L  G  L  K  I  C  G  F  L  Q  R  T  N  S  L  E  E  K
AGAAAACTGGGGCTCAAGATCTGCGGCTTCTTGCAAAGGACCAACAGCCTGGAAGAGAAG  180

S  R  L  V  S  A  F  K  E  R  Q  S  S  K  N  L  L  S  C  E
AGTCGCCTTGTGAGTGCCTTCAAGGAGAGGCAATCCTCCAAGAACCTGCTTTCCTGTGAA  240

N  S  D  R  D  A  R  F  R  R  T  E  T  D  F  S  N  L  F  A
AACAGCGACCGGGATGCCCGCTTCCGGCGCACAGAGACTGACTTCTCTAATCTGTTTGCT  300

R  D  L  L  P  A  K  N  G  E  E  Q  T  V  Q  F  L  L  E  V
AGAGATCTGCTTCCGGCTAAGAACGGTGAGGAGCAAACCGTGCAATTCCTCCTGGAAGTG  360

V  D  I  L  L  N  Y  V  R  K  T  F  D  R  S  T  K  V  L  D
GTGGACATACTCCTCAACTATGTCCGCAAGACATTTGATCGCTCCACCAAGGTGCTGGAC  420

F  H  H  P  H  Q  L  L  E  G  M  E  G  F  N  L  E  L  S  D
TTTCATCACCCACACCAGTTGCTGGAAGGCATGGAGGGCTTCAACTTGGAGCTCTCTGAC  480

H  P  E  S  L  E  Q  I  L  V  D  C  R  D  T  L  K  Y  G  V
CACCCCGAGTCCCTGGAGCAGATCCTGGTCGACTGCAGAGACACCTTGAAGTATGGGGTT  540

R  T  G  H  P  R  F  F  N  Q  L  S  T  G  L  D  I  I  G  L
CGCACAGGTCATCCTCGATTTTTCAACCAGCTCTCCACTGGATTGGATATTATTGGCCTA  600

A  G  E  W  L  T  S  A  N  T  N  M  F  T  Y  E  I  A  P
GCTGGAGAATGGCTGACATCAACGGCCAATACCAACATGTTCACATATGAAATTGCACCA  660

V  F  V  L  M  E  Q  I  T  L  K  K  M  R  E  I  V  G  W  S
GTGTTTGTCCTCATGGAACAAATAACACTTAAGAAGATGAGAGAGATAGTTGGATGGTCA  720

S  K  D  G  D  G  I  F  S  P  G  G  A  I  S  N  M  Y  S  I
AGTAAAGATGGTGATGGGATATTTTCTCCTGGGGGCGCCATATCCAACATGTACAGCATC  780

M  A  A  R  Y  K  Y  F  P  E  V  K  T  K  G  M  A  A  V  P
ATGGCTGCTCGCTACAAGTACTTCCCCGGAAGTTAAGACAAAGGGCATGGCGGCTGTGCCT  840

K  L  V  L  F  T  S  E  Q  S  H  Y  S  I  K  K  A  G  A  A
AAACTGGTCCTCTTCACCTCAGAACAGAGTCACTATTCCATAAAGAAAGCTGGGGCTGCA  900

L  G  F  G  T  D  N  V  I  L  I  K  C  N  E  R  G  K  I  I
CTTGGCTTTGGAACTGACAATGTGATTTTGATAAAGTGCAATGAAAGGGGGAAAATAATT  960

P  A  D  F  E  A  K  I  L  E  A  K  Q  K  G  Y  V  P  F  Y
CCAGCTGATTTTGAGGCAAAAATTCTTGAAGCCAAACAGAAGGGATATGTTCCCTTTTAT 1020
```

FIG. 7A

```
         V  N  A  T  A  G  T  T  V  Y  G  A  F  D  P  I  Q  E  I  A
       GTCAATGCAACTGCTGGCACGACTGTTTATGGAGCTTTTGATCCGATACAAGAGATTGCA  1080
         D  I  C  E  K  Y  N  L  W  L  H  V  D  A  A  W  G  G  G  L
       GATATATGTGAGAAATATAACCTTTGGTTGCATGTCGATGCTGCCTGGGGAGGTGGGCTG  1140
         L  M  S  R  K  H  R  H  K  L  N  G  I  E  R  A  N  S  V  T
       CTCATGTCCAGGAAGCACCGCCATAAACTCAACGGCATAGAAAGGGCCAACTCAGTCACC  1200
         N  N  P  H  K  M  M  G  V  L  L  Q  C  S  A  I  L  V  K  E
       TGGAACCCTCACAAGATGATGGGCGTGCTGTTGCAGTGCTCTGCCATTCTCGTCAAGGAA  1260
         K  G  I  L  Q  G  C  N  Q  M  C  A  G  Y  L  F  Q  P  D  K
       AAGGGTATACTCCAAGGATGCAACCAGATGTGTGCAGGATACCTCTTCCAGCCAGACAAG  1320
         Q  Y  D  V  S  Y  D  T  G  D  K  A  I  Q  C  G  R  M  V  D
       CAGTATGATGTCTCCTACGACACCGGGGACAAGGCAATTCAGTGTGGCCGCCACGTGGAT  1380
         I  F  K  F  W  L  M  W  K  A  K  G  T  V  G  F  E  N  Q  I
       ATCTTCAAGTTCTGGCTGATGTGGAAAGCAAAGGGCACAGTGGGATTTGAAAACCAGATC  1440
         N  K  C  L  E  L  A  E  Y  L  Y  A  K  I  K  N  R  E  E  F
       AACAAATGCCTGGAACTGGCTGAATACCTCTATGCCAAGATTAAAAACAGAGAAGAATTT  1500
         E  M  V  F  N  G  E  P  E  H  T  N  V  C  F  W  Y  I  P  Q
       GAGATGGTTTTCAATGGCGAGCCTGAGCACACAAACGTCTGTTTTTGGTATATTCCACAA  1560
         S  L  R  G  V  P  D  S  P  Q  R  R  E  K  L  H  K  V  A  P
       AGCCTCAGGGGTGTGCCAGACAGCCCTCAACGACGGGAAAAGCTACACAAGGTGGCTCCA  1620
         K  I  K  A  L  M  M  E  S  G  T  T  M  V  G  Y  Q  P  Q  G
       AAAATCAAAGCCCTGATGATGGAGTCAGGTACGACCATGGTTGGCTACCAGCCCCAAGGG  1680
         D  K  A  N  F  F  R  M  V  I  S  N  P  A  A  T  Q  S  D  I
       GACAAGGCCAACTTCTTCCGGATGGTCATCTCCAACCCAGCCGCTACCCAGTCTGACATT  1740
         D  F  L  I  E  E  I  E  R  L  G  Q  D  L  *
       GACTTCCTCATTGAGGAGATAGAAAGACTGGGCCAGGATCTGTAA                 1785
```

FIG. 7B

```
  M  A  S  S  T  P  S  S  S  A  T  S  S  N  A  G  A  D  P  N
ATGGCGTCTTCGACCCCATCTTCGTCCGCAACCTCCTCGAACGCGGGAGCGGACCCCAAT    60

T  T  N  L  R  P  T  T  Y  D  T  W  C  G  V  A  H  G  C  T
ACCACTAACCTGCGCCCCACAACGTACGATACCTGGTGCGGCGTGGCCCATGGATGCACC   120

R  K  L  G  L  K  I  C  G  F  L  Q  R  T  N  S  L  E  E  K
AGAAAACTGGGGCTCAAGATCTGCGGCTTCTTGCAAAGGACCAACAGCCTGGAAGAGAAG   180

S  R  L  V  S  A  F  K  E  R  Q  S  S  K  N  L  L  S  C  E
AGTCGCCTTGTGAGTGCCTTCAAGGAGAGGCAATCCTCCAAGAACCTGCTTTCCTGTGAA   240

N  S  D  R  D  A  R  F  R  R  T  E  T  D  F  S  N  L  F  A
AACAGCGACCGGGATGCCCGCTTCCGGCGCACAGAGACTGACTTCTCTAATCTGTTTGCT   300

R  D  L  L  P  A  K  N  G  E  E  Q  T  V  Q  F  L  L  E  V
AGAGATCTGCTTCCGGCTAAGAACGGTGAGGAGCAAACCGTGCAATTCCTCCTGGAAGTG   360

V  D  I  L  L  N  Y  V  R  K  T  F  D  R  S  T  K  V  L  D
GTGGACATACTCCTCAACTATGTCCGCAAGACATTTGATCGCTCCACCAAGGTGCTGGAC   420

F  H  H  P  H  Q  L  L  E  G  M  E  G  F  N  L  E  L  S  D
TTTCATCACCCACACCAGTTGCTGGAAGGCATGGAGGGCTTCAACTTGGAGCTCTCTGAC   480

H  P  E  S  L  E  Q  I  L  V  D  C  R  D  T  L  K  Y  G  V
CACCCCGAGTCCCTGGAGCAGATCCTGGTCGACTGCAGAGACACCTTGAAGTATGGGGTT   540

R  T  G  H  P  R  F  F  N  Q  L  S  T  G  L  D  I  I  G  L
CGCACAGGTCATCCTCGATTTTTCAACCAGCTCTCCACTGGATTGGATATTATTGGCCTA   600

A  G  E  W  L  T  S  T  A  N  T  N  M  F  T  Y  E  I  A  P
GCTGGAGAATGGCTGACATCAACGGCCAATACCAACATGTTCACATATGAAATTGCACCA   660

V  F  V  L  M  E  Q  I  T  L  K  K  M  R  E  I  V  G  W  S
GTGTTTGTCCTCATGGAACAAATAACACTTAAGAAGATGAGAGAGATAGTTGGATGGTCA   720

S  K  D  G  D  G  I  F  S  P
AGTAAAGATGGTGATGGGATATTTTCTCCT                                 750
```

FIG.8

```
        T  A  N  T  N  M  F  T  Y  E  I  A  P  V  F  V  L  M  E  Q
       ACGGCCAATACCAACATGTTCACATATGAAATTGCACCAGTGTTTGTCCTCATGGAACAA    681

I  T  L  K  K  M  R  E  I  V  G  W  S  S  K  D  G  D  G  I
       ATAACACTTAAGAAGATGAGAGAGATAGTTGGATGGTCAAGTAAAGATGGTGATGGGATA    741

F  S  P  G  G  A  I  S  N  M  Y  S  I  M  A  A  R  Y  K  Y
       TTTTCTCCTGGGGGCGCCATATCCAACATGTACAGCATCATGGCTGCTCGCTACAAGTAC    801

F  P  E  V  K  T  K  G  M  A  A  V  P  K  L  V  L  F  T  S
       TTCCCGGAAGTTAAGACAAAGGGCATGGCGGCTGTGCCTAAACTGGTCCTCTTCACCTCA    861

E  Q  S  H  Y  S  I  K  K  A  G  A  A  L  G  F  G  T  D  N
       GAACAGAGTCACTATTCCATAAAGAAAGCTGGGGCTGCACTTGGCTTTGGAACTGACAAT    921

V  I  L  I  K  C  N  E  R  G  K  I  I  P  A  D  F  E  A  K
       GTGATTTTGATAAAGTGCAATGAAAGGGGGAAAATAATTCCAGCTGATTTTGAGGCAAAA    981

I  L  E  A  K  Q  K  G  Y  V  P  F  Y  V  N  A  T  A  G  T
       ATTCTTGAAGCCAAACAGAAGGGATATGTTCCCTTTTATGTCAATGCAACTGCTGGCACG   1041

T  V  Y  G  A  F  D  P  I  Q  E  I  A  D  I  C  E  K  Y  N
       ACTGTTTATGGAGCTTTTGATCCGATACAAGAGATTGCAGATATATGTGAGAAATATAAC   1101

L  W  L  H  V  D  A  A  W  G  G  G  L  L  M  S  R  K  H  R
       CTTTGGTTGCATGTCGATGCTGCCTGGGGAGGTGGGCTGCTCATGTCCAGGAAGCACCGC   1161

H  K  L  N  G  I  E  R  A  N  S  V  T  W  N  P  H
       CATAAACTCAACGGCATAGAAAGGGCCAACTCAGTCACCTGGAACCCTCAC             1212
```

FIG.9

```
          G   I   E   R   A   N   S   V   T   N   N   P   H   K   M   M   G   V   L   L
          GGCATAGAAAGGGCCAACTCAGTCACCTGGAACCCTCACAAGATGATGGGCGTGCTGTTG  1233

Q   C   S   A   I   L   V   K   E   K   G   I   L   Q   G   C   N   Q   M   C
          CAGTGCTCTGCCATTCTCGTCAAGGAAAAGGGTATACTCCAAGGATGCAACCAGATGTGT  1293

A   G   Y   L   F   Q   P   D   K   Q   Y   D   V   S   Y   D   T   G   D   K
          GCAGGATACCTCTTCCAGCCAGACAAGCAGTATGATGTCTCCTACGACACCGGGGACAAG  1353

A   I   Q   C   G   R   H   V   D   I   F   K   F   W   L   M   W   K   A   K
          GCAATTCAGTGTGGCCGCCACGTGGATATCTTCAAGTTCTGGCTGATGTGGAAAGCAAAG  1413

G   T   V   G   F   E   N   Q   I   N   K   C   L   E   L   A   E   Y   L   Y
          GGCACAGTGGGATTTGAAAACCAGATCAACAAATGCCTGGAACTGGCTGAATACCTCTAT  1473

A   K   I   K   N   R   E   E   F   E   M   V   F   N   G   E   P   E   N   T
          GCCAAGATTAAAAACAGAGAAGAATTTGAGATGGTTTTCAATGGCGAGCCTGAGCACACA  1533

N   V   C   F   W   Y   I   P   Q   S   L   R   G   V   P   D   S   P   Q   R
          AACGTCTGTTTTTGGTATATTCCACAAAGCCTCAGGGGTGTGCCAGACAGCCCTCAACGA  1593

R   E   K   L   H   K   V   A   P   K   I   K   A   L   M   M   E   S   G   T
          CGGGAAAAGCTACACAAGGTGGCTCCAAAAATCAAAGCCCTGATGATGGAGTCAGGTACG  1653

T   M   V   G   Y   Q   P   Q   G   D   K   A   N   F   F   R   M   V   I   S
          ACCATGGTTGGCTACCAGCCCCAAGGGGACAAGGCCAACTTCTTCCGGATGGTCATCTCC  1713

N   P   A   A   T   Q   S   D   I   D   F   L   I   E   E   I   E   R   L   G
          AACCCAGCCGCTACCCAGTCTGACATTGACTTCCTCATTGAGGAGATAGAAAGACTGGGC  1773

Q   D   L   *
          CAGGATCTGTAA                                                  1785
```

FIG. 10

```
  M   A   S   S   T   P   S   S   S   A   T   S   S   N   A   G   A   D   P   N
ATGGCGTCTTCGACCCCATCTTCGTCCGCAACCTCCTCGAACGCGGGAGCGGACCCCAAT   60

T   T   N   L   R   P   T   T   Y   D   T   W   C   G   V   A   H   G   C   T
ACCACTAACCTGCGCCCCACAACGTACGATACCTGGTGCGGCGTGGCCCATGGATGCACC  120

R   K   L   G   L   K   I   C   G   F   L   Q   R   T   N   S   L   E   E   K
AGAAAACTGGGGCTCAAGATCTGCGGCTTCTTGCAAAGGACCAACAGCCTGGAAGAGAAG  180

S   R   L   V   S   A   F   K   E   R   Q   S   S   K   N   L   L   S   C   E
AGTCGCCTTGTGAGTGCCTTCAAGGAGAGGCAATCCTCCAAGAACCTGCTTTCCTGTGAA  240

N   S   D   R   D   A   R   F   R   R   T   E   T   D   F   S   N   L   F   A
AACAGCGACCGGGATGCCCGCTTCCGGCGCACAGAGACTGACTTCTCTAATCTGTTTGCT  300

R   D   L   L   P   A   K   N   G   E   E   Q   T   V   Q   F   L   L   E   V
AGAGATCTGCTTCCGGCTAAGAACGGTGAGGAGCAAACCGTGCAATTCCTCCTGGAAGTG  360

V   D   I   L   L   N   Y   V   R   K   T   F   D   R   S   T   K   V   L   D
GTGGACATACTCCTCAACTATGTCCGCAAGACATTTGATCGCTCCACCAAGGTGCTGGAC  420

F   H   H   P   H   Q   L   L   E   G   M   E   G   F   N   L   E   L   S   D
TTTCATCACCCACACCAGTTGCTGGAAGGCATGGAGGGCTTCAACTTGGAGCTCTCTGAC  480

H   P   E   S   L   E   Q   I   L   V   D   C   R   D   T   L   K   Y   G   V
CACCCCGAGTCCCTGGAGCAGATCCTGGTCGACTGCAGAGACACCTTGAAGTATGGGGTT  540

R   T   G   H   P   R   F   F   N   Q   L   S   T   G   L   D   I   I   G   L
CGCACAGGTCATCCTCGATTTTTCAACCAGCTCTCCACTGGATTGGATATTATTGGCCTA  600

A   G   E   W   L   T   S   T   A   N   T   N   M   F   T   Y   E   I   A   P
GCTGGAGAATGGCTGACATCAACGGCCAATACCAACATGTTCACATATGAAATTGCACCA  660

V   F   V   L   M   E   Q   I   T   L   K   K   M   R   E   I   V   G   W   S
GTGTTTGTCCTCATGGAACAAATAACACTTAAGAAGATGAGAGAGATAGTTGGATGGTCA  720

S   K   D   G   D   G   I   F   S   P   G   G   A   I   S   N   M   Y   S   I
AGTAAAGATGGTGATGGGATATTTTCTCCTGGGGGCGCCATATCCAACATGTACAGCATC  780

M   A   A   R   Y   K   Y   F   P   E   V   K   T   K   G   M   A   A   V   P
ATGGCTGCTCGCTACAAGTACTTCCCGGAAGTTAAGACAAAGGGCATGGCGGCTGTGCCT  840

K   L   V   L   F   T   S   E   Q   S   H   Y   S   I   K   K   A   G   A   A
AAACTGGTCCTCTTCACCTCAGAACAGAGTCACTATTCCATAAAGAAAGCTGGGGCTGCA  900

L   G   F   G   T   D   N   V   I   L   I   K   C   N   E   R   G   K   I   I
CTTGGCTTTGGAACTGACAATGTGATTTTGATAAAGTGCAATGAAAGGGGGAAAATAATT  960

P   A   D   F   E   A   K   I   L   E   A   K   Q   K   G   Y   V   P   F   Y
CCAGCTGATTTTGAGGCAAAAATTCTTGAAGCCAAACAGAAGGGATATGTTCCCTTTTAT 1020
```

FIG. 11A

```
        V  N  A  T  A  G  T  T  V  Y  G  A  F  D  P  I  Q  E  I  A
      GTCAATGCAACTGCTGGCACGACTGTTTATGGAGCTTTTGATCCGATACAAGAGATTGCA  1080

D  I  C  E  K  Y  N  L  W  L  H  V  D  A  A  W  G  G  G  L
      GATATATGTGAGAAATATAACCTTTGGTTGCATGTCGATGCTGCCTGGGGAGGTGGGCTG  1140

L  M  S  R  K  H  R  H  K  L  N  G  I  E  R  A  N  S  V  T
      CTCATGTCCAGGAAGCACCGCCATAAACTCAACGGCATAGAAAGGGCCAACTCAGTCACC  1200

N  N  P  H  K  M  M  G  V  L  L  Q  C  S  A  I  L  V  K  E
      TGGAACCCTCACAAGATGATGGGCGTGCTGTTGCAGTGCTCTGCCATTCTCGTCAAGGAA  1260

K  G  I  L  Q  G  C  N  Q  M  C  A  G  Y  L  F  Q  P  D  K
      AAGGGTATACTCCAAGGATGCAACCAGATGTGTGCAGGATACCTCTTCCAGCCAGACAAG  1320

Q  Y  D  V  S  Y  D  T  G  D  K  A  I  Q  C  G  R  M  V  D
      CAGTATGATGTCTCCTACGACACCGGGGACAAGGCAATTCAGTGTGGCCGCCACGTGGAT  1380

I  F  K  F  W  L  M  W  K  A  K  G  T  V  G  F  E  N  Q  I
      ATCTTCAAGTTCTGGCTGATGTGGAAAGCAAAGGGCACAGTGGGATTTGAAAACCAGATC  1440

N  K  C  L  E  L  A  E  Y  L  Y  A  K  I  K  N  R  E  E  F
      AACAAATGCCTGGAACTGGCTGAATACCTCTATGCCAAGATTAAAAACAGAGAAGAATTT  1500

E  M  V  F  N  G  E  P  E  H  T  N  V  C  F  W  Y  I  P  Q
      GAGATGGTTTTCAATGGCGAGCCTGAGCACACAAACGTCTGTTTTTGGTATATTCCACAA  1560

S  L  R  G  V  P  D  S  P  Q  R  R  E  K  L  H  K  V  A  P
      AGCCTCAGGGGTGTGCCAGACAGCCCTCAACGACGGGAAAAGCTACACAAGGTGGCTCCA  1620

K  I  K  A  L  M  M  E  S  G  T  T  M  V  G  Y  Q  P  Q  G
      AAAATCAAAGCCCTGATGATGGAGTCAGGTACGACCATGGTTGGCTACCAGCCCCAAGGG  1680

D  K  A  N  F  F  R  M  V  I  S  N  P  A  A  T  Q  S  D  I
      GACAAGGCCAACTTCTTCCGGATGGTCATCTCCAACCCAGCCGCTACCCAGTCTGACATT  1740

D  F  L  I  E  E  I  E  R  L  G  Q  D  L  *
      GACTTCCTCATTGAGGAGATAGAAAGACTGGGCCAGGATCTGTAA                 1785
```

FIG.11B

METHOD FOR THE DIAGNOSIS AND TREATMENT OF GLUTAMIC ACID DECARBOXYLASE AUTOANTIGEN ASSOCIATED DISEASES

CROSS REFERENCE TO RELATED APPLICATIONS

This is continuation of U.S. patent application Ser. No. 08/308,952 filed Sep. 20, 1994, now U.S. Pat. No. 5,837,812, issued Nov. 17, 1998, which is a file wrapper continuation of U.S. patent application Ser. No. 07/839,805 filed Feb. 21, 1992 now abandoned.

FIELD OF INVENTION

The present invention relates to the identification, cloning and sequencing of nucleic acid molecules encoding an isoform of the enzyme glutamic acid decarboxylase and further relates to the use of these molecules and/or peptides and polypeptides encoded thereby in diagnostic tests for Insulin Dependent Diabetes Mellitus and other diseases in which glutamic acid decarboxylase is an autoantigen and in the treatment of patients suffering from these diseases.

BACKGROUND TO THE INVENTION

The enzyme glutamic acid decarboxylase (hereinafter referred to as "GAD") catalyses the conversion of L-glutamic acid to the inhibitory neurotransmitter γ-amino butyric acid (hereinafter referred to as "GABA"). GAD is expressed both in the GABA secretory neurons of the central nervous system (1–3), in the β-cells of the pancreas (4,5), and in spermatoza (6). Analysis of immunoaffinity-purified, enzymatically active brain GAD has identified several isomeric forms of GAD with $M_r$ 54–67,000 (7,8). Using antisera raised to purified brain GAD to screen brain cDNA expression libraries, cDNAs encoding full length rat (9) and feline (10) GAD sequences have been isolated and sequenced. Comparisons of the deduced amino acid sequences of rat and feline GAD show that both proteins are 95% identical and, therefore, highly conserved during evolution.

Autoantibodies reactive with GAD in GABA-ergic neurons are present in the majority of sera from patients with the rare neurological disease Stiff Man Syndrome (hereinafter referred to "SMS"; 11,12). Patients positive for GAD autoantibodies have an increased frequency of polyendocrine autoimmunity especially Insulin Dependent Diabetes Mellitus (hereinafter referred to as "IDDM"). During the pre-clinical stage of IDDM and in patients with recent onset clinical IDDM, autoantibodies are frequently detected against an islet cell $M_r$ 64,000 protein designated "64K" (13). In a recent report, the 64K autoantigen was presumptively identified as GAD (14). However, Genovese (15) has suggested that GAD is co-precipitated with a separate 64K protein, the latter distinguished by tryptic products of $M_r$ 37,000/40,000 that are distinct from a $M_r$ 50,000 product of GAD. GAD comprises at least two isoforms encoded by separate genes (16, 17, 18). The predicted molecular weights of the known isoforms are approximately 67,000 and 65,000 (referred to as the "67K" and "65K" isoforms, respectively). The distribution of GAD isoforms in different tissues in still not well defined, but it is likely that the 65K isoform accounts for the GAD component of the 64K autoantigen (17).

In work leading up to the present invention, the inventors sought to clone the 67K isoform of GAD from human and other species for potential diagnostic and/or therapeutic use. In accordance with the present invention, human brain (HB), human pancreatic islet (HI) and mouse brain (MB) GAD (hereinafter referred to as "HBGAD", "HIGAD" and "MEGAD", respectively) have been cloned and sequenced. In further accordance with the present invention, recombinant GAD proteins corresponding to the 67K isoform and their fragments and derivatives were used as an antigen to detect antibodies and T-cells reactive with GAD thereby forming a basis for a new range of diagnostics and therapeutics for diseases of the type including preclinical and clinical IDDM and SMS and other diseases in which GAD is an autoantigen.

SUMMARY OF THE INVENTION

Accordingly, a first aspect of the present invention provides a nucleic acid molecule comprising a nucleotide sequence which encodes or is complementary to a sequence which encodes human or mouse glutamic acid decarboxylase (GAD) corresponding to a 67K isoform of the enzyme or antigenically active fragments or derivatives thereof.

Another aspect of the present invention provides a synthetic peptide or polypeptide displaying the antigenicity of all or a portion of the 67K isoform of GAD or a fragment thereof and reactive with autoantibodies and/or T-cells.

Yet another aspect of the present invention contemplates a method for the detection of antibodies to GAD in a sample which method comprises contacting a peptide or polypeptide corresponding to all or an antigenic portion of the 67K isoform of GAD with said sample for a time and under conditions sufficient for a complex to form between the peptide or polypeptide and an antibody reactive to GAD and then detecting the complex Still yet another aspect of the present invention provides a method for detecting diseases of the type including IDDM and SMS, or for screening asymptomatic individuals, by the detection and/or determination of the titre of autoantibodies in a biological sample from said individual, said method comprising contacting said sample with a peptide or polypeptide corresponding to all or an antigenic portion of the 67K isoform of GAD for a time and under conditions sufficient to form a complex between the peptide or polypeptide and an antibody reactive to GAD and then detecting the complex and/or the amount of peptide or polypeptide which has been bound in a complex.

Even yet another method of reducing autoantibodies and/or autoreactive T-cells to GAD in a patient in need thereof and/or to desensitise or induce tolerance to eliminate or diminish reactivity of autoreactive T-cells or autoantibodies to the autoantigen, said method comprising administering to said patient an effective amount of an antigenic peptide or polypeptide corresponding to all or part of the 67K isoform of GAD.

The present invention also provides a method of reducing autoantibodies and/or autoreactive T-cells to GAD in a patient in need thereof and/or to desensitise or induce tolerance to eliminate or diminish reactivity of autoreactive T-cells or autoantibodies to the autoantigen, said method comprising administering to said patient GAD reactive T-cell lines or clones or cell membranes and/or receptors for the antigen from said GAD reactive T-cell lines or clones for a time and under conditions sufficient to act as immunogens to induce inhibition and/or reduction of T-cells responses to GAD autoantigen.

BRIEF DESCRIPTION OF THE FIGURES

FIG. 1 shows a comparison of the 540 nucleotide DNA sequences corresponding to human brain GAD (HBGAD)

(SEQ ID NO:1) and human islet GAD (HIGAD) (SEQ ID NO:2) excluding oligonucleotide sequences.

FIG. 2 shows the deduced amino acid sequences of HBGAD (SEQ ID NO:3) and HIGAD (SEQ ID NO:4) and their alignment with the equivalent region in the feline GAD (SEQ ID NO:5) (amino acids 218–398).

FIG. 3 shows the nucleotide sequence and deduced amino acid sequence corresponding to the full length mouse brain GAD (MBGAD) SEQ ID NO:6 and SEQ ID NO:7, respectively.

FIG. 4 shows the nucleotide sequence and deduced amino acid sequence corresponding to the N-terminal fragment of MBGAD designated MBGAD12 SEQ ID NO:8 and SEQ ID NO:9, respectively that encodes amino acids 1–204 of the published feline GAD sequence (10).

FIG. 5 shows the nucleotide sequence and deduced amino acid sequence corresponding to the mid-region fragment of MBGAD, designated MBGAD34 SEQ ID NO:10 and (SEQ ID NO:11, respectively corresponding to amino acids 198–404 of the published feline GAD sequence.

FIG. 6 shows the nucleotide sequence and deduced amino acid sequence corresponding to the C-terminal fragment of MBGAD, designated MBGAD56 SEQ ID NO:12 and SEQ ID NO:13, respectively corresponding to amino acids 392–593 of the published feline GAD sequence.

FIG. 7 shows the full length nucleotide sequence and deduced amino acid sequence corresponding to human brain GAD (HBGAD-FL) SEQ ID NO:14 and SEQ ID NO:15, respectively.

FIG. 8 shows the nucleotide sequence and deduced amino acid sequence corresponding to the N-terminal fragment of HBGAD, designated HBGAD17 SEQ ID NO:16 and SEQ ID NO:17, respectively corresponding to amino acids 1–250 of the published feline GAD sequence.

FIG. 9 shows the nucleotide sequence and deduced amino acid sequence corresponding to the mid region fragment of HBGAD or HIGAD, designated HBGAD14 or HIGAD14 SEQ ID NO:18 and SEQ ID NO:19, respectively corresponding to amino acids 208–404 of the published feline GAD sequence.

FIG. 10 shows the nucleotide sequence and deduced amino acid sequence corresponding to the C-terminal region fragment of HBGAD, designated HBGAD65 SEQ ID NO:20 and SEQ ID NO:21, respectively corresponding to amino acid 392–594 of the published feline GAD sequence.

FIG. 11 shows the full length nucleotide sequence and deduced amino acid sequence corresponding to human islet GAD (HIGAD-FL) SEQ ID NO:22 and SEQ ID NO:23, respectively.

DETAILED DESCRIPTION OF THE INVENTION

The present invention provides a nucleic acid molecule comprising a nucleotide sequence which encodes or is complementary to a sequence which encodes human or mouse glutamic acid decarboxylase (GAD) corresponding to a 67K isoform of the enzyme or antigenically active fragments or derivatives thereof.

By the "67K isoform" is meant the form of GAD having approximately $M_r$ 67,000 and/or any fragments, derivatives, homologues and/or immunological relatives thereof and which are distinguishable and/or otherwise distinct from the $M_r$ 65,000 form of GAD and which reacts preferentially to T-cells and/or autoantibodies from individuals with clinical or preclinical IDDM, SMS and/or other similar diseases.

Preferably, the GAD is human pancreatic islet GAD (HIGAD), human brain cell GAD (HBGAD) and/or mouse brain cell GAD (MBGAD). Preferably, the nucleic acid molecule is DNA, at least a part of which has a nucleotide sequence substantially corresponding to the sequence shown in FIGS. 1, 3, 7 and/or 11 or a fragment, derivative, homologue or or immunological relative thereof or one or more sequences complementary thereto. The present invention, however also extends to any single or multiple nucleotide substitutions, deletions and/or additions to the sequence shown in FIGS. 1, 3, 7 and/or 11 and which still encode a GAD or fragment or derivative thereof having the requisite antigenic profile and reactive with autoantibodies or T-cells. Furthermore, when the nucleic acid molecule is RNA, the ribonucleotide sequence will, in a preferred embodiment, be substantially complementary to one or more of the sequences shown in FIGS. 1, 3, 7 and/or 11 or a fragment, derivative, or homolgue thereof.

The present invention also provides a recombinant nucleic acid (e.g. DNA) molecule comprising a nucleotide sequence as described above operably linked to an expression control sequence. Such a recombinant molecule may, for example, comprise an expression vector. The present invention further extends to a host cell such as a bacterium, yeast, mammalian or insect cell transformed with such a recombinant molecule. A preferred mammalian cell line is the Chinese Hamster Ovary (CHO) cell line.

Another aspect of this invention is directed to a synthetic (e.g. recombinant) peptide or polypeptide displaying the antigenicity of all or a portion of an isoform of GAD which is reactive with autoantibodies and/or T-cells.

Such a synthetic peptide or polypeptide may, for example, be prepared by recombinant means such as by the expression of a host cell transformed with the recombinant molecules described above. The peptide or polypeptide may be fused to another peptide or polypeptide. Alternatively, it may be prepared by chemical synthesis, such as by the well-known Merrifield solid-phase synthesis procedure. The synthetic (eg. recombinant) peptide or polypeptide may or may not retain GAD enzymatic activity. Furthermore, although synthetic GAD or fragments thereof represent a preferred embodiment, the present invention also extends to biologically pure preparations of the naturally occurring enzyme or its fragments. By "biologically pure" is meant a preparation of at least 60%, preferably at least 70%, more preferably at least 80% and still more. preferably at least 90% by weight enzyme.

In a most preferred embodiment, the present invention extends to naturally occurring or synthetic peptide or polypeptides corresponding to MBGAD, HIGAD and/or HBGAD and to nucleotide sequences coding for same as well as to fragments, derivatives, homolgoues or immunological relatives thereof. By way of example, such fragments are shown in FIGS. 2, 4, 5, 6, 8, 9 and 10. By "derivatives" is meant to include any single or multiple amino acid substitution, deletion and/or addition relative to the naturally occurring sequence or to the sequence as shown in FIGS. 1, 3, 7 and/or 11 and including any single or multiple substitution, deletion and/or addition to other molecules associated with the peptide or polypeptide including carbohydrate lipid and/or other proteinacious moieties. Such derivatives, therefore, include glycosylated or non-glycosylated forms or molecules with altered glycosylation patterns.

The present invention also contemplates a method for the detection of autoantibodies associated with IDDM which method comprises contacting a peptide or polypeptide corresponding to all, or an antigenic portion of, GAD, which GAD corresponds to the 67K isoform of the enzyme, or a fragment or derivative thereof with a biological sample from a patient to be tested for a time and under conditions sufficient for a complex to form between the peptide or polypeptide and an antibody reactive to GAD and then detecting the complex. Preferably, the biological sample is serum. Even more preferably, the peptide or polypeptide is immobilised onto a solid support before, during or after contact with the serum. Methods of detection are well known and include colorimetric, fluorometric and radioactive procedures. Other detection means can also be used such as involving agglutination. This assay can be varied in any number of ways without departing from the scope of the present invention.

The present invention also extends to the use of a peptide or polypeptide corresponding to the 67K isoform of GAD, or antigenic fragments thereof, as an antigen in a diagnostic test for diseases of the type including IDDM and SMS, or for screening asymptomatic individuals by detection or determination of the titre of antibodies in a patient's serum, for example using ELISA or RIA technology or an agglutination assay using antigen-coated beads or the like.

This aspect of the present invention may conveniently be carried out by the detection and/or determination of the titre of autoantibodies in a biological sample (e.g. serum) from a human subject, said method comprising contacting said sample with a peptide or polypeptide corresponding to an antigenic portion of the 67K isoform of GAD or a fragment or derivative thereof for a time and under conditions sufficient for a complex to form between the peptide or polypeptide and an antibody reactive to GAD and then detecting the complex and/or amount of peptide or polypeptide which has been bound in the complex. Preferably, the peptide or polypeptide is immobilised onto a solid support before, during or after contact with the sample and the peptide or polypeptide is as hereinbefore defined.

Alternatively, such diseases may be detected or at least a negative result re-confirmed or otherwise by screening for GAD associated immune complexes. It is possible, for example, that a negative autoantibody result could have been caused by autoantibodies forming complexes with GAD thereby not being available for binding in the aforementioned assay. To conveniently detect GAD immune complexes, serum or other biological fluid is contacted with an anti-GAD antibody (e.g. a monoclonal antibody) for a time and under conditions sufficient for a GAD-autoantibody immune complex to bind.

Preferably, the anti-GAD antibody is first immobilised onto a solid support. An anti-immunoglobulin antibody, generally with a label or other reporter molecule attached, is then used to screen for the antibody component of the GAD complex.

One skilled in the art will immediately recognise that the assays as contemplated herein may be modified without departing from the scope of the present invention. All such modifications and variations of these assays are encompassed by the present invention.

The invention also extends to use of the peptides and/or polypeptides, or fragments, or derivatives of the present invention in the treatment of patients. In this later aspect, such methods of treatment include their use as an adsorbent to remove autoantibodies or autoreactive cells from a patient, their use in direct administration to a patient as a means of desensitising or inducing tolerance to eliminate or diminish reactivity of autoreactive T-cells or autoantibodies to the IDDM autoantigen or to generate T-cell lines or clones to be used for or as therapeutic agents.

As contemplated herein, the method of treatment includes but is not limited to the following examples of treatment. A first example of treatment is desensitisation or tolerance induction using an effective amount of GAD peptide or polypeptide or fragments thereof to alter T-cell recognition of GAD and induce T-cell suppression. This may be achieved by using the known effect of certain ultraviolet wavelengths, especially UV-B, to modify antigen presentation through the skin (see 19). Effective amounts of GAD peptide or polypeptide or fragments thereof would be applied epicutaneously to the skin of subjects exhibiting peripheral blood T-cell reactivity to GAD, after exposure of skin to UV-B radiation. Treatment would be repeated until such time that T-cell reactivity to GAD was suppressed. A second treatment involves application of GAD to the skin together with one or more cytokines such as but not limited to TNF$\alpha$ or $\beta$. A third treatment involves T-cell immunisation whereby T-cell lines are generated to GAD peptide or polypeptide or fragments thereof by standard procedures, cells attenuated by fixation with agents such as glutaraldehyde or paraformaldehyde, washed under sterile conditions and re-injected to patients for a time and under conditions causing suppression of the endogenous T-cell response to GAD. These approaches of treatment are applicable to the prevention of clinical IDDM in asymptomatic subjects with preclinical IDDM or subjects with recent onset clinical IDDM, as well as to the recurrence of IDDM in subjects who have received pancreas, islet cell or insulin-producing cell transplants. These approaches are also applicable to SMS and other diseases where GAD is an autoantigen. In accordance with the present invention the effective amount of GAD peptide or polypeptide is 0.1 $\mu$g to 10 mg per dose and preferably 1.0 $\mu$g to 1 mg per dose. A dose may comprise a single administration or an administration protocol. Administration may be by any convenient means such as, but not limited to, intravenous, subcutaneous, epicutaneous, infusion, oral, topical, intranasal, supository or intraperitoneal administration. The GAD peptide or polypeptide may be administered alone or in combination with one or more other active molecules, molecules which facilitate the GAD peptide or polypeptide activity such as cytokines, and in particular, TNF-$\alpha$ and/or TNF-$\beta$.

In yet a further embodiment, the present invention contemplates the use of a peptide or polypeptide corresponding to the 67K isoform of GAD, or antigenic fragments or derivatives thereof, to measure reactivity of a patient's cells to the IDDM autoantigen. The peptide or polypeptide, or fragments or derivatives thereof, may be added, in solution or bound to a solid support together with cells from a patient derived from peripheral blood or from tissue biopsies either unfractionated, fractionated or derived as a continuous cell line. Reactivity to the autoantigen may then be measured by standard proliferation assays such as incorporation of tritiated thymidine, standard cytotoxic assays such as release of marker radioactivity from target cells, measurements of expressed or secreted molecules such as cytokines or other standard assays of cellular reactivity which are well known in the art.

In one embodiment of this aspect of this invention there is provided a diagnostic kit for assaying patient T-cells. Standard 96 well plates, as used in ELISA assays, are pre-coated with a monoclonal antibody (MAb) to a T-cell cytokine such as $\gamma$-interferon ($\gamma$-IFN) with or without antigen. Alternatively, antigen is added in soluble form together with aliquots of peripheral blood mononuclear cells or T-cells. Incubation is allowed to proceed for two or more days, the cells are washed off, wells washed again and plates developed with a labelled second MAb to the cytokine such as anti-γ-IFN conjugated with alkaline phosphatase or horseradish peroxidase. Colorimetric reaction and read-out systems can then be utilised. Alternatively, it is possible to visualise microscopically individual spots on bottoms of wells representing cytokine produced at the single T-cell level, thereby enabling the precursor frequency of antigen-reactive T-cells to be determined.

The present invention encompasses other forms of kits and diagnostic assays including a kit comprising a container adapted to contain a synthetic peptide or polypeptide corresponding to the 67 isoform of GAD or its fragments, derivatives, homologues and/or immunological relatives. The kit may contain a second container adapted to contain or receive a sample to be tested. A third container may be present adapted to contain reagents for detecting GAD-antibody complexes. Alternatively, where the kit is to detect GAD immune complexes, the kit may comprise one or more containers (e.g. wells) adapted to contain a GAD specific antibody (e.g. a monoclonal antibody). Additional containers with the kit may then contain recepticles for receiving fluid samples and a labelled antibody.

In further accordance with the present invention, expression of the cDNA insert encoding the GAD's described herein or fragments thereof, may be achieved in a number of different ways.

As an example, successful expression of the autoantigen as a fusion protein can be achieved using the pGEX vectors which give expression of glutathione S-transferase fusion proteins, using *E. coli* as the host cells. Expression could also be achieved, by way of example, using the well-known pEV vectors or the polyhistidine expression vectors (23) again using *E. coli* as the host cells. Alternatively, GAD may be expressed as a non-fused polypeptide, by using appropriate vector and host cell combinations. Other vector and host cell combinations which can be used in accordance with the present invention including a number of well described yeast shuttle vectors for use in yeast cells, or eukaryotic vectors useful in continuous cell lines, (eg. CHO cells) or transgenic animals.

The present invention will now be further described with reference to the following non-limiting Examples.

EXAMPLE 1

Materials and Methods

Mouse RNA. Mouse RNA was obtained from brains of BALB/C mice.

Human RNA. RNA was obtained from human adult brain and pancreatic islets. Islets were isolated from a donor pancreas by an intraductal collagenase distension procedure. Individually hand-picked islets were lysed in 5 M guanidinium isothiocynate, 10 mM Tris pH 7.6, 10 mM EDTA and RNA purified by centrifugation through a 5.7M CsCl cushion. Total RNA from human brain was a gift of Claude Bernard from Latrobe University School of Behavioural Science, Australia.

Human cDNA libraries. Two λgt-11 based human cDNA expression libraries were used as a source of GAD cDNA. A brain-stem cDNA library was purchased from Clonetech and the islet-cell library was a gift of Alan Permutt from the Washington School of Medicine, St. Louis. cDNA was prepared from phage stocks by a plate lysis method (20).

Polymerase chain reaction (PCR). Based on the published rat (9) and feline (10) GAD cDNA sequences, oligonucleotide primers were designed from conserved regions. The primers used to Isolate the various clones are shown in Table 1. First strand synthesis of total RNA (1 μg) was performed in 10 mM Tris pH 8.3, 50 mM KCl, 1.5 mM $MgCl_2$, 100 μM dNTPs (PCR buffer) containing 2 pmole of complimentary primer, 40 U of RNasin and 5 U of MoMLV reverse transcriptase at 37° C. for 30 min in a 50 ul reaction volume. λgt-11 cDNA (100 ng) or 10 μl of the first strand reaction was amplified in PCR buffer containing 20 pmole of each primer and 2.5 U of TaqI polymerase by 30 thermal cycles (one cycle: 1.5 min at 95° C.; 2.0 min at 37–45° C.; 2.0 min at 72° C.). Reactions were analysed on low melting agarose gels and products of the expected size purified by phenol extraction (20).

Cloning and DNA sequencing. PCR amplified DNA fragments were cloned into the plasmid expression vector pGEX 1·3(21) and also into the histidine expression vector pDS56, (−1) and (−2) (23). Nucleotide sequence was determined by the dideoxy chain termination method (22) using the M13 universal primer and specific primers designed from internal GAD sequence, as described in Table 1.

TABLE 1

ORIGIN OF GAD cDNA CLONES

| GAD CLONE | AA REGION EQUIVALENT TO FELINE GAD | PCR SOURCE | OLIGONUCLEOTIDES 5'–3' |
|---|---|---|---|
| MBGAD 12 | 1–204 | BRAIN RNA | RGAD1-(SEQ ID NO:24) ATTGGATCCACCGAGCTGATGGCGTCTTC |
| | | | RGAD2-(SEQ ID NO:25) CCGAATTCGCCATTCGCCAGCTAAACC |
| MBGAD34 | 198–404 | BRAIN RNA | RGAD3-(SEQ ID NO:26) ATTGGATCCGGTTTAGCTGGCGAATGGC |
| | | | RGAD4-(SEQ ID NO:27) CCGAATTCTGTGAGGGTTCCAGGTGAC |
| MBGAD56 | 392–593 | BRAIN RNA | RGAD5-(SEQ ID NO:28) ATTGGATCCGTCACCTGGAACCCTCACA |
| | | | RGAD6-(SEQ ID NO:29) CCGAATTCATTACAGATCCTGGCCCA |
| HBGAD | 208–404 | BRAIN cDNA LIBRARY | GAD1-(SEQ ID NO:30) ACTGCCAATACCAATATGTTCACATATGA |
| | | | RGAD4-(SEQ ID NO:21) CCGAATTCTGTGAGGGTTCCAGGTGAC |
| HIGAD | 208–404 | ISLET cDNA LIBRARY | GAD1-(SEQ ID NO:28) ACTGCCAATACCAATATGTTCACATATGA |
| | | | RGAD4-CCGAATTCTGTQAGGGTTCCAGGTGAC |
| HBGAD17 | 1–250 | BRAIN RNA | RGAD1-(SEQ ID NO:29) ATTGGATCCACCGAGCTGATGGCGTCTTC |
| | | | GAD7-(SEQ ID NO:30) GGAGAAAATATCCCATCACC |
| HBGAD14 | 208–404 | BRAIN RNA | GAD1-ACTGCCAATACCAATATGT-TCACATATGA |

TABLE 1-continued

ORIGIN OF GAD cDNA CLONES

| GAD CLONE | AA REGION EQUIVALENT TO FELINE GAD | PCR SOURCE | OLIGONUCLEOTIDES 5'–3' |
|---|---|---|---|
| HBGAD65 | 392–594 | BRAIN RNA | RGAD4-(SEQ ID NO:31) CCGAATTCTGTCAGGGTTCCAGGTGAC<br>GAD6-(SEQ ID NO:32) ATTGGATCCGGCATAGAAAGGGCCAA<br>GAD5-(SEQ ID NO:33) CCCATAAACTCATGTTCTTG |
| HBGAD-FL | 1–594 | BRAIN RNA | RGAD1-ATTGGATCCACCGAGCTGATGGCGTCTTC |
| HBGAD-FL | 1–594 | PANCREAS RNA | GAD5-(SEQ ID NO:33) CCCATAAACTCATGTTCTTG |
| HIGAD14 | 208–404 | ISLET RNA | GAD1-ACTGCCAATACCAATATGTTCACATATGA<br>RGAD4-CCGMTTCTGTGAGGGTTCCAGGTGAC |

EXAMPLE 2

Cloning of Human GAD

To clone human GAD cDNA, oligonucleotide pairs overlapping nucleotide stretches conserved between rat and feline sequences were synthesised and used in PCR reactions to amplify cDNA extracted from brain and islet λgt-11 expression libraries as well as from RNA extracted from human brain or human islets. In extensive PCR reactions using various combinations of oligonucleotide primers and temperatures of annealing, a product of 600 nucleotides was obtained from both brain and islet cDNA templates with the oligonucleotides primers: 5' ACTGCCAATACCAATATGT-TCACATATGA 3' and 5' CCGAATTCTGTAGAGGGTTC-CAGGTGAC 3' (complementary, contains an Eco RI site) which would correspond to nucleotide positions 739–768 and 1312–1330 of the published feline cDNA (10), respectively, representing the middle portion of the GAD open reading frame. The two 600 nucleotide PCR products were digested with EcoRI and SmaI ligated with pGEX-3X DNA cleaved with EcoRI and SmaI and transformed into *E. coli*. Restriction analysis of plasmid DNA from transformants identified a human brian GAD clone (HBGAD) and an islet GAD clone (HIGAD).

The 540 nucleotide DNA sequences determined for both HBGAD and HIGAD, excluding the oligonucleotide sequences, are shown in FIG. 1. These two sequences display 90% similarity with the feline GAD sequence and therefore, confirm the identity of the human clones. Alignment of the HBGAD sequence with the HIGAD sequence showed that they were identical except for four nucleotide changes at position 88 (T-A), 91(T-C) 128(C-T) and 366(C-T).

FIG. 2 shows the deduced amino acid sequences of HBGAD and HIGAD and their alignment with the corresponding region in the feline GAD protein (aa 218–393). The four nucleotide differences between HBGAD and HIGAD would result in three conservative amino acid changes at residues 247 (leucine→isoleucine) and 260 (threonine→isoleucine) and 248 (phenylalanine→leucine); residue 339 (leucine) remains unchanged because the nucleotide difference at position 366 is silent. These amino acid differences between the middle one-third of the brain and islet GAD proteins provide evidence for the existence of isomeric forms of GAD in human tissue.

Infiltration of the pancreatic islets with mononuclear cells culminates in the destruction of insulin-producing β cells and clinical IDDM (20). The enzyme GAD has recently been identified as a putative islet autoantigen in IDDM based on the ability of several IDDM sera to co-precipitate the 64K islet cell protein and GAD (14) and it has been shown that peripheral blood T cells from subjects with pre-clinical and clinical IDDM can be activated by islet membrane preparations containing the 64K autoantigen and GAD (24, 25). The finding of sequence differences between brain and islet GAD may now provide a genetic basis for selective autoimmune destruction of pancreatic islets.

EXAMPLE 3

Construction of a Full Length Human Brain and Islet GAD cDNA

Normal brain RNA was reverse-transcribed with either GAD 5 (5' CCCATAAACTCATGTTCTTG 3') or GAD 7 (5' GGAGAAAAATATCCCATCACC 3') oligonucleotides. As shown in Table 1, amplification of the GAD7 and GAD5 first strand products by PCR using GAD specific oligonucleotides generated a cDNA encoding aa 1–250 HBGAD17 and an overlapping cDNA that encodes aa 208–594. One hundred nanograms of each fragment was denatured at 95° C. in PCR buffer and hybrid molecules extended and amplified using RGAD 1 and GAD 5 oligonucleotides that anneal at the end of the hybridised molecules (Table 1) to generate a full length human GAD clone that encodes the 594aa GAD open reading frame to generate a full length HBGAD and HIGAD (FIGS. 7 and 11).

EXAMPLE 4

Cloning of Mouse Brain GAD

Mouse Brain GAD was cloned as described above for HBGAD and HIGAD except that primers RGAD1 and RGAD6 (Table 1) were used.

EXAMPLE 5

T-Cell Responses to Recombinant Proteins 67 subjects were tested for their T-cell response to HBGAD and HIGAD.

Subject backgrounds were as follows:

15 Recent onset clinical Diabetics (less than 3 months after onset of symptoms)

44 Pre-clinical Diabetics (asymptomatic first degree relatives of a person with IDDM who are positive for islet cell antibodies that react with islets in frozen sections of human pancreas)

8 Controls (normal healthy young adults)

Peripheral blood mononuclear cells (PBMC) were separated by Ficoll Hypaque density gradient centrifugation, and washed twice. The cells were then resuspended ($2 \times 10^6$ ml) in complete culture medium (RPMI 1640 with Hepes buffer 20 mM, penicillin 100 units/ml, streptomycin 100 μl/ml, $10^{-5}$M 2-mercaptoethanol and 5% autologous serum) and seeded (200 μl/well) into 96 well round-bottomed microtitre plates. The recombinant GAD fusion proteins HBGAD are HIGAD which contain the 196 amino acid middle portions of human brain and human islet GAD respectively, as described in Table 1 were added to final concentrations of 10, 1.0 and 0.1 μg/ml, together with and glutathione-S-transferase (GST) to which the recombinant GAD antigen is fused. Sonicated fetal pig islets, which the present inventors have shown to contain GAD (24), as well as fetal pig liver, thyroid and kidney were also used as sources of antigen(s).

The cultures were incubated for 5 days in a humidified 5% $CO_2$ atmosphere with the addition of $^3$H-thymidine (1 μCi/well) for the last 17 hours. The cells were then harvested for scintillation counting. Median counts per minute (cpm) of each quadruplicate were used to derive stimulation indices, ie. cpm with antigen/cpm without antigen. A positive result was defined as a stimulation index greater than that obtained with GST (recombinant GAD proteins or greater than 2.0 (fetal tissues).

TABLE 2

Reactivity of Peripheral Blood T-cells

| | Antigens | | |
|---|---|---|---|
| Subject group | H islet GAD14 | H brain GAD14 | Fetal pig proislets |
| Recent onset clinical diabetes | 10/15 | 8/14 | 5/12 |
| Preclinical diabetes | 25/44 | 18/36 | 16/34 |
| Controls | 3/8 | 3/8 | 1/8 |

The results shown in Table 2 indicate that overall, 35/59 (59%) recent onset or preclinical subjects have circulating T-cells capable of proliferating in response to human islet GAD and (26/50) 52% to human brain GAD.

EXAMPLE 6

Antibody Responses to Recombinant Proteins

Sera samples from subjects were tested for an antibody response to the N-terminal fragment of recombinant murine brain GAD, MBGAD12 as well as against the full length recombinant human brain GAD.

Protein Used As Antigen

Recombinant mouse brain GAD12 was cloned and expressed as a fusion protein with glutathione-S-transferase (GST) in the pOEX system. MBGAD12 was cleaved with thrombin and the GAD portion affinity purified from GST using glutathione agarose beads. MBGAD34, MBGAD56, HBGAD17 and HBGAD65 were cloned and expressed as fusion proteins with six histidine residues at the N-terminus using the polyhistidine expression system.

ELISAS

In all ELISA assays, the recombinant GAD proteins, were coated at 1 μg/mL on plastic wells of a 96-well plate, wells were exposed to blocking buffer, washed and incubated with doubling dilutions of test sera, washed and exposed to alkaline phosphatase-conjugated second antibody, washed, developed with n-nitrophenol chromogen and read at 405 nM. An OD>mean+2 SD with control sera was taken as positive.

Subject Patients were as follows:

The results of ELISA using MBGAD12, MBGAD34 and MBGAD56, and HBGAD17 and HBGAD65 are shown in Tables 3 and 4, respectively:

TABLE 3

| | MBGAD12 | MBGAD34 | MBGAD56 |
|---|---|---|---|
| Preclinical IDDM | 5/9 | 5/9 | 4/9 |
| Recent onset Clinical IDDM | 2/13 | 4/13 | 3/13 |
| Controls | 0/22 | 0/20 | 0/20 |

Seven of nine (78%) preclinical IDDM and six of 13 (46%) recent-onset IDDM sera reacted with at least one of the MBGAD peptides. Only three of nine (33%) and one of 13 (8%) preclinical and recent onset IDDM sera, respectively, reacted with all three MBGAD fragments. None of the three GAD peptides was recognised preferentially by either sera group. These findings indicate that patterns of sera reactivity with recombinant MBGAD are heterogenous and that at least three major epitopes exist in the GAD67 isoform.

TABLE 4

| SUBJECTS | HBGAD 17 | HBGAD65 |
|---|---|---|
| Pre-clinical IDDM | 7/9 | 3/9 |
| Recent onset IDDM | 3/7 | 3/7 |
| Controls | 0/16 | 0/16 |

The results using the two human brain GAD fragments HBGAD17 and HBGAD65 in an ELISA format are comparable with those obtained using the equivalent mouse brain GAD peptides MBGAD12 and MBGAD56.

Those skilled in the art will appreciate that the invention described herein is susceptible to variations and modifications other than susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

1. Roberts, E., Chase, T. N., and Tower, D. B. (1976) Kroc Foundation Series, Vol 5; GABA in Nervous System Function, Raven Press, New York.
2. Mugaini, E., and Oertel, W. H. (1985). In Handbook of Chemical Neuroanatomy (A. Bjorklund and T. Hokfelt, Eds.) Vol 4, pp 436–608 Elsevier, N.Y.
3. Blessing, W. W. (1990) Neuroscience 37, 171–185.
4. Okada, Y., Taniguchi. H., and Shimada, C. (1976) Science 194, 620–622.
5. Garry, D. J., Appel, N. M., Carry, M. G., and Sorensen, R. L. (1988) J. Histochem. Cytochem. 36, 573–580.
6. Persson, H., Pelto-Huikko, M., Metsis, M., Soder, O., Brene, S., Skog, S., Hokfelt, T., and Ritzen, E. M. (1990) Mol. Cell. Biol. 19, 4701–4711.
7. Gottlieb, D. I., Chang, Y-C., and Schwob, J. E. 9186) Proc. Natl. Acad. Sci USA. 83, 8808–8812.
8. Chang, Y-C., and Gottlieb, D. L. (1988) J. Neuroscience 8, 2123–2130.
9. Julien, J-F., Samana, P., and Mallet, J. (1990) J. Neurochemistry 54, 703–705.
10. Kobayashi, Y., Kaufman, D. L. and Tobin, A. J. (1987) J. Neuroscience 7, 2768–2772.
11. Solimena, M., Folli, F., Denis-Donini, S., Comi, G. C., Pozza, G., DeCamilli, P., and Vicari, A. M. (1988) N. Engl. J. Med. 318,1012–1020.

12. Solimena, M., Folli, F., Aparisi, R., Pozza, G., and DeCamilli, P. (1990) N. Engl. J. Med. 322, 1555–1560.
13. Baekkeskov, S., Nielson, J. H. Marner, B., Bilde, T., Ludvigsson, J., and Lernmark, A. (1982) Nature 298, 167–169.
14. Baekkeskov, S., Aanstoot, H-J., Christgau, S., Reetz, A., Solimena, S., Cascalho, M., Folli, F., Richter-Olesen, H., and DeCamilli P. (1990) Nature 347, 151–156.
15. Genovese, S., Cassidy, D., Bonifacio, E., Bottazzo, G. F. and Christie, M. R. (1991) Diab. Clin. Res. Prac. 14(Suppl 1), S11.
16. Cram, D. S., Barnett, L. D., Joseph, J. L. and Harrison, L. C. (1991) Biochem. Biophys. Res. Commun. 176, 1239–1244.
17. Karlsen, A. E., Hagopian, W. Z., Crubin, C. E. et. al. (1991) Proc. Natl. Acad. Sci. USA. 88, 8337–8341.
18. Erlander, M. G., Tillakaratne, N. J. K., Feldblum, S., Patel, N. and Tobin, A. J. (1991) Neuron 7, 91–100.
19. Ullrich S. E., Yee, C. K., Kripke, M. L. (1986) Immunology 58, 158–190.
20. Sambrook, J., Fritsch, E. F., and Maniatis, T. (1989) In Molecular Cloning. A Laboratory Manual. Vol 1–3, Cold Spring Harbor Laboratory Press, Cold Spring Harbor, N.Y.
21. Smith, D. B., and Johnson, K. S. (1988) Gene 67, 31–40.
22. Sanger, F., Nicklen, S., and Coulson, A. R. (1977) Proc. Natl. Acad. Sci. USA. 74, 5463–5467.
23. Hochuli, E., Bamworth, W., Dobeli, H., Gentz, R. and Stuber, D. (1988) Biotechnology 6 1321–1325.
24. Harrison, L. C., De Aizpurua, H., Loudovaris, T., Campbell, I. L. Cebon, J. S., Tait, B. D., Colman, P. G. (1991) Diabetes 40, 1128–1133.
25. Harrison, L. C., Chu, X. S., De Aizpurua, H. J., Graham, M., Honeyman, M. C., Colman, P. G. (1992) J. Clin. Invest. (in press).

What is claimed is:

1. An isolated nucleic acid molecule comprising the nucleotide sequence of human pancreatic islet GAD (HIGAD) SEQ ID NO:2.

2. An isolated nucleic acid molecule comprising the nucleotide sequence of human brain GAD (HBGAD) SEQ ID NO:1.

3. An isolated nucleic acid molecule comprising the nucleotide sequence of mouse brain GAD (MBGAD) SEQ ID NO:6.

4. An isolated nucleic acid molecule comprising the nucleotide sequence of HBGAD-FL (SEQ ID NO:14).

5. An isolated nucleic acid molecule comprising the nucleotide sequence of HIGAD-FL (SEQ ID NO:22).

6. An isolated nucleic acid molecule comprising the nucleotide sequence of MBGAD34 (SEQ ID NO:10).

7. An isolated nucleic acid molecule comprising the nucleotide sequence of MBGAD56 (SEQ ID NO:12).

8. An isolated nucleic acid molecule comprising the nucleotide sequence of HBGAD17 (SEQ ID NO:16).

9. An isolated nucleic acid molecule comprising the nucleotide sequence of HBGAD14 (SEQ ID NO:18).

10. An isolated nucleic acid molecule comprising the nucleotide sequence of HBGAD65 (SEQ ID NO:20).

11. A vector containing the isolated nucleic acid sequence of any one of claims 1–10.

* * * * *

SEQUENCE LISTING

```
<160> NUMBER OF SEQ ID NOS: 34

<210> SEQ ID NO 1
<211> LENGTH: 543
<212> TYPE: DNA
<213> ORGANISM: Unknown Organism
<220> FEATURE:
<223> OTHER INFORMATION: Description of Unknown Organism: Human Brain
      GAD

<400> SEQUENCE: 1
attgcacccg tgtttgttct catggaacag attactctta agaagatgag aaagatcgtt      60
ggatggtcaa ataaagatgg tgatgggtta ttttctcctg ggggagccat atccaatatg     120
tacagcacca tggctgctcg ttacaagtac ttcccagaag tgaagacaaa aggcatggcg     180
gctgtgccca aactggtcct cttcacctca gaacacagtc actattccat aaagaaagcc     240
ggggctgcgc ttggctttgg aaccgacaat gtgattttga taaagtgcaa tgaaaggggg     300
aagataattc cggctgattt agaggcaaaa attcttgatg ccaaacaaaa gggctatgtt     360
cccctctatg tcaatgcaac cgcaggcacg actgtttacg gagcattcga tccaatccag     420
gaaattgcgg acatatgtga gaaatacaac ctttggctgc atgtggatgc tgcctgggt      480 ggtggactgc tcatgtcccg gaagcaccgc cacaaactca gcggcataga aagggccaat     540
tca                                                                    543

<210> SEQ ID NO 2
<211> LENGTH: 543
<212> TYPE: DNA
<213> ORGANISM: Unknown Organism
<220> FEATURE:
<223> OTHER INFORMATION: Description of Unknown Organism: Human islet
      GAD

<400> SEQUENCE: 2
attgcacccg tgtttgttct catggaacag attactctta agaagatgag aaagatcgtt      60
ggatggtcaa ataaagatgg tgatgggtta ttttctcctg ggggagccat atccaatatg     120
tacagcacca tggctgctcg ttacaagtac ttcccagaag tgaagacaaa aggcatggcg     180
gctgtgccca aactggtcct cttcacctca gaacacagtc actattccat aaagaaagcc     240
ggggctgcgc ttggctttgg aaccgacaat gtgattttga taaagtgcaa tgaaaggggg     300
```

```
aagataattc cggctgattt agaggcaaaa attcttgatg ccaaacaaaa gggctatgtt        360
cccctctatg tcaatgcaac cgcaggcacg actgtttacg gagcattcga tccaatccag        420
gaaattgcgg acatatgtga gaaatacaac ctttggctgc atgtggatgc tgcctggggt        480
ggtggactgc tcatgtcccg gaagcaccgc acaaaactca gcggcataga aagggccaat        540
tca                                                                      543
```

```
<210> SEQ ID NO 3
<211> LENGTH: 181
<212> TYPE: PRT
<213> ORGANISM: Unknown Organism
<220> FEATURE:
<223> OTHER INFORMATION: Description of Unknown Organism: Amino Acid
      Sequence of Human Brain GAD

<400> SEQUENCE: 3
```

Ile Ala Pro Val Phe Val Leu Met Glu Gln Ile Thr Leu Lys Lys Met
 1               5                  10                  15

Arg Lys Ile Val Gly Trp Ser Asn Lys Asp Gly Asp Gly Leu Phe Ser
            20                  25                  30

Pro Gly Gly Ala Ile Ser Asn Met Tyr Ser Thr Met Ala Ala Arg Tyr
        35                  40                  45

Lys Tyr Phe Pro Glu Val Lys Thr Lys Gly Met Ala Ala Val Pro Lys
    50                  55                  60

Leu Val Leu Phe Thr Ser Glu His Ser His Tyr Ser Ile Lys Lys Ala
65                  70                  75                  80

Gly Ala Ala Leu Gly Phe Gly Thr Asp Asn Val Ile Leu Ile Lys Cys
                85                  90                  95

Asn Glu Arg Gly Lys Ile Ile Pro Ala Asp Leu Glu Ala Lys Ile Leu
            100                 105                 110

Asp Ala Lys Gln Lys Gly Tyr Val Pro Leu Tyr Val Asn Ala Thr Ala
        115                 120                 125

Gly Thr Thr Val Tyr Gly Ala Phe Asp Pro Ile Gln Glu Ile Ala Asp
    130                 135                 140

Ile Cys Glu Lys Tyr Asn Leu Trp Leu His Val Asp Ala Ala Trp Gly
145                 150                 155                 160

Gly Gly Leu Leu Met Ser Arg Lys His Arg His Lys Leu Ser Gly Ile
                165                 170                 175

Glu Arg Ala Asn Ser
            180

```
<210> SEQ ID NO 4
<211> LENGTH: 181
<212> TYPE: PRT
<213> ORGANISM: Unknown Organism
<220> FEATURE:
<223> OTHER INFORMATION: Description of Unknown Organism: Amino Acid
      Sequence of Human Islet GAD

<400> SEQUENCE: 4
```

Ile Ala Pro Val Phe Val Leu Met Glu Gln Ile Thr Leu Lys Lys Met
 1               5                  10                  15

Arg Lys Ile Val Gly Trp Ser Asn Lys Asp Gly Asp Gly Ile Leu Ser
            20                  25                  30

Pro Gly Gly Ala Ile Ser Asn Met Tyr Ser Ile Met Ala Ala Arg Tyr
        35                  40                  45

Lys Tyr Phe Pro Glu Val Lys Thr Lys Gly Met Ala Ala Val Pro Lys

```
              50                  55                  60
Leu Val Leu Phe Thr Ser Glu His Ser His Tyr Ser Ile Lys Lys Ala
 65                  70                  75                  80

Gly Ala Ala Leu Gly Phe Gly Thr Asp Asn Val Ile Leu Ile Lys Cys
                 85                  90                  95

Asn Glu Arg Gly Lys Ile Ile Pro Ala Asp Leu Glu Ala Lys Ile Leu
                100                 105                 110

Asp Ala Lys Gln Lys Gly Tyr Val Pro Leu Tyr Val Asn Ala Thr Ala
            115                 120                 125

Gly Thr Thr Val Tyr Gly Ala Phe Asp Pro Ile Gln Glu Ile Ala Asp
        130                 135                 140

Ile Cys Glu Lys Tyr Asn Leu Trp Leu His Val Asp Ala Ala Trp Gly
145                 150                 155                 160

Gly Gly Leu Leu Met Ser Arg Lys His Arg His Lys Leu Ser Gly Ile
                165                 170                 175

Glu Arg Ala Asn Ser
            180

<210> SEQ ID NO 5
<211> LENGTH: 181
<212> TYPE: PRT
<213> ORGANISM: Unknown Organism
<220> FEATURE:
<223> OTHER INFORMATION: Description of Unknown Organism: Feline Brain
      GAD

<400> SEQUENCE: 5

Ile Ala Pro Val Phe Val Leu Met Glu Gln Ile Thr Leu Lys Lys Met
 1               5                  10                  15

Arg Glu Ile Val Gly Trp Ser Ser Lys Asp Gly Asp Gly Ile Phe Ser
                 20                  25                  30

Pro Gly Gly Ala Ile Ser Asn Met Tyr Ser Ile Met Ala Ala Arg Tyr
             35                  40                  45

Lys Phe Phe Pro Glu Val Lys Thr Lys Gly Met Ala Ala Val Pro Lys
         50                  55                  60

Leu Val Leu Phe Thr Ser Glu His Ser His Tyr Ser Ile Lys Lys Ala
 65                  70                  75                  80

Gly Ala Ala Leu Gly Phe Gly Thr Asp Asn Val Ile Leu Ile Lys Cys
                 85                  90                  95

Asn Glu Arg Gly Lys Ile Ile Pro Ala Asp Leu Glu Ala Lys Ile Leu
                100                 105                 110

Glu Ala Lys Gln Lys Gly Tyr Val Pro Leu Tyr Val Asn Ala Thr Ala
            115                 120                 125

Gly Thr Thr Val Tyr Gly Ala Phe Asp Pro Ile Gln Glu Ile Ala Asp
        130                 135                 140

Ile Cys Glu Lys Tyr Asn Leu Trp Leu His Val Asp Ala Ala Trp Gly
145                 150                 155                 160

Gly Gly Leu Leu Met Ser Arg Lys His Arg His Lys Leu Ser Gly Ile
                165                 170                 175

Glu Arg Ala Asn Ser
            180

<210> SEQ ID NO 6
<211> LENGTH: 1782
<212> TYPE: DNA
<213> ORGANISM: Unknown Organism
<220> FEATURE:
```

-continued

```
<223> OTHER INFORMATION: Description of Unknown Organism: Full Length
      Mouse Brain GAD
<220> FEATURE:
<221> NAME/KEY: CDS
<222> LOCATION: (1)..(1779)

<400> SEQUENCE: 6 atg gcg tct tcc act cct tcg cct gca acc tcc tcg aac gcg gga gcg        48
Met Ala Ser Ser Thr Pro Ser Pro Ala Thr Ser Ser Asn Ala Gly Ala
 1               5                  10                  15 gat cct aat act acc aac ctg cgc cct aca acg tat gat act tgg tgt        96
Asp Pro Asn Thr Thr Asn Leu Arg Pro Thr Thr Tyr Asp Thr Trp Cys
             20                  25                  30 ggc gta gcc cat gga tgc acc aga aaa ctg ggc ctg aag atc tgt ggc       144
Gly Val Ala His Gly Cys Thr Arg Lys Leu Gly Leu Lys Ile Cys Gly
         35                  40                  45 ttc tta caa agg acc aat agc ctg gaa gag aag agt cgt ctt gtg agc       192
Phe Leu Gln Arg Thr Asn Ser Leu Glu Glu Lys Ser Arg Leu Val Ser
     50                  55                  60 gcc ttc agg gag agg cag tcc tcc aag aac ctg ctt tcc tgt gaa aac       240
Ala Phe Arg Glu Arg Gln Ser Ser Lys Asn Leu Leu Ser Cys Glu Asn
 65                  70                  75                  80 agt gac cag ggt gcc cgc ttc cgg cgc aca gag acc gac ttc tcc aac       288
Ser Asp Gln Gly Ala Arg Phe Arg Arg Thr Glu Thr Asp Phe Ser Asn
                 85                  90                  95 ctg ttt gct caa gat ctg ctt cca gct aag aac ggg gag gag caa act       336
Leu Phe Ala Gln Asp Leu Leu Pro Ala Lys Asn Gly Glu Glu Gln Thr
            100                 105                 110 gcg cag ttc ttg ctg gaa gtg gta gac ata ctc ctc aac tat gtc cgc       384
Ala Gln Phe Leu Leu Glu Val Val Asp Ile Leu Leu Asn Tyr Val Arg
        115                 120                 125 aag aca ttt gat cgc tcc acc aag gtt ctg gat ttc cac cac cca cac       432
Lys Thr Phe Asp Arg Ser Thr Lys Val Leu Asp Phe His His Pro His
    130                 135                 140 cag ttg ctg gaa ggc atg gaa ggc ttt aat ttg gag ctg tct gac cac       480
Gln Leu Leu Glu Gly Met Glu Gly Phe Asn Leu Glu Leu Ser Asp His
145                 150                 155                 160 ccc gag tct ctg gag cag atc ctg gtt gac tgt aga gac acc ctg aag       528
Pro Glu Ser Leu Glu Gln Ile Leu Val Asp Cys Arg Asp Thr Leu Lys
                165                 170                 175 tac ggg gtt cgc aca ggt cac cct cga ttt ttc aac cag ctc tct act       576
Tyr Gly Val Arg Thr Gly His Pro Arg Phe Phe Asn Gln Leu Ser Thr
            180                 185                 190 ggt ttg gat atc att ggt tta gct ggc gaa tgg ctg aca tcg act gcc       624
Gly Leu Asp Ile Ile Gly Leu Ala Gly Glu Trp Leu Thr Ser Thr Ala
        195                 200                 205 aat acc aat atg ttc aca tat gaa att gca ccc gtg ttt gtt ctc atg       672
Asn Thr Asn Met Phe Thr Tyr Glu Ile Ala Pro Val Phe Val Leu Met
    210                 215                 220 gaa cag att act ctt aag aag atg aga aag atc gtt gga tgg tca aat       720
Glu Gln Ile Thr Leu Lys Lys Met Arg Lys Ile Val Gly Trp Ser Asn
225                 230                 235                 240 aaa gat ggt gat ggg ata ttt tct cct ggg gga gcc ata tcc aat atg       768
Lys Asp Gly Asp Gly Ile Phe Ser Pro Gly Gly Ala Ile Ser Asn Met
                245                 250                 255 tac agc atc atg gct gct cgt tac aag tac ttc cca gaa gtg aag aca       816
Tyr Ser Ile Met Ala Ala Arg Tyr Lys Tyr Phe Pro Glu Val Lys Thr
            260                 265                 270 aaa ggc atg gcg gct gtg ccc aaa ctg gtc ctc ttc acc tca gaa cac       864
Lys Gly Met Ala Ala Val Pro Lys Leu Val Leu Phe Thr Ser Glu His
        275                 280                 285
```

```
agt cac tat tcc ata aag aaa gcc ggg gct gcg ctt ggc ttt gga acc      912
Ser His Tyr Ser Ile Lys Lys Ala Gly Ala Ala Leu Gly Phe Gly Thr
    290             295                 300 gac aat gtg att ttg ata aag tgc aat gaa agg ggg aag ata att ccg      960
Asp Asn Val Ile Leu Ile Lys Cys Asn Glu Arg Gly Lys Ile Ile Pro
305                 310                 315                 320 gct gat tta gag gca aaa att ctt gat gcc aaa caa aag ggc tat gtt     1008
Ala Asp Leu Glu Ala Lys Ile Leu Asp Ala Lys Gln Lys Gly Tyr Val
                325                 330                 335 ccc ctt tat gtc aat gca acc gca ggc acg act gtt tac gga gca ttc     1056
Pro Leu Tyr Val Asn Ala Thr Ala Gly Thr Thr Val Tyr Gly Ala Phe
            340                 345                 350 gat cca atc cag gaa att gcg gac ata tgt gag aaa tac aac ctt tgg     1104
Asp Pro Ile Gln Glu Ile Ala Asp Ile Cys Glu Lys Tyr Asn Leu Trp
        355                 360                 365 ctg cat gtg gat gct gcc tgg ggt ggt gga ctg ctc atg tcc cgg aag     1152
Leu His Val Asp Ala Ala Trp Gly Gly Gly Leu Leu Met Ser Arg Lys
    370                 375                 380 cac cgc cac aaa ctc agc ggc ata gaa agg gcc aat tca gtc acc tgg     1200
His Arg His Lys Leu Ser Gly Ile Glu Arg Ala Asn Ser Val Thr Trp
385                 390                 395                 400 aac cct cac aag atg atg ggc gtg ctc ctc cag tgc tct gcc att ctg     1248
Asn Pro His Lys Met Met Gly Val Leu Leu Gln Cys Ser Ala Ile Leu
                405                 410                 415 gtc aag gaa aag ggt ata ctc caa gga tgc aac cag atg tgt gca ggc     1296
Val Lys Glu Lys Gly Ile Leu Gln Gly Cys Asn Gln Met Cys Ala Gly
            420                 425                 430 tac ctc ttc cag cca gac aag cag tat gac gtc tcc tat gac acc ggg     1344
Tyr Leu Phe Gln Pro Asp Lys Gln Tyr Asp Val Ser Tyr Asp Thr Gly
        435                 440                 445 gac aag gcg att cag tgt ggc cgc cat gtg gac atc ttc aag ttc tgg     1392
Asp Lys Ala Ile Gln Cys Gly Arg His Val Asp Ile Phe Lys Phe Trp
    450                 455                 460 ctg atg tgg aaa gca aag ggc acc gtg gga ttt gaa aac cag atc aac     1440
Leu Met Trp Lys Ala Lys Gly Thr Val Gly Phe Glu Asn Gln Ile Asn
465                 470                 475                 480 aaa tgc ctg gag ctg gct gat tac ctc tac gcc aag att aaa aac aga     1488
Lys Cys Leu Glu Leu Ala Asp Tyr Leu Tyr Ala Lys Ile Lys Asn Arg
                485                 490                 495 gaa gag ttt gag atg gtt ttc gat ggt gag cct gag cac aca aat gtc     1536
Glu Glu Phe Glu Met Val Phe Asp Gly Glu Pro Glu His Thr Asn Val
            500                 505                 510 tgt ttc tgg tac att cca caa agc ctt cga ggg gtt cca gat agc cct     1584
Cys Phe Trp Tyr Ile Pro Gln Ser Leu Arg Gly Val Pro Asp Ser Pro
        515                 520                 525 gag cga cga gaa aag cta cac agg gtg gct ccc aag atc aaa gct ctg     1632
Glu Arg Arg Glu Lys Leu His Arg Val Ala Pro Lys Ile Lys Ala Leu
    530                 535                 540 atg atg gag tca gga aca acc atg gtg ggc tac cag cct caa ggg gac     1680
Met Met Glu Ser Gly Thr Thr Met Val Gly Tyr Gln Pro Gln Gly Asp
545                 550                 555                 560 aag gcc aac ttc ttc cgg atg gtc atc tct aac cca gcc gcc acc cag     1728
Lys Ala Asn Phe Phe Arg Met Val Ile Ser Asn Pro Ala Ala Thr Gln
                565                 570                 575 tct gac atc gat ttc ctc att gag gag ata gag agg ttg ggc cag gat     1776
Ser Asp Ile Asp Phe Leu Ile Glu Glu Ile Glu Arg Leu Gly Gln Asp
            580                 585                 590 ctg taa                                                              1782
Leu
```

<210> SEQ ID NO 7
<211> LENGTH: 593
<212> TYPE: PRT
<213> ORGANISM: Unknown Organism
<220> FEATURE:
<223> OTHER INFORMATION: Description of Unknown Organism: Full Length Mouse Brain GAD

<400> SEQUENCE: 7

```
Met Ala Ser Ser Thr Pro Ser Pro Ala Thr Ser Ser Asn Ala Gly Ala
 1               5                  10                  15

Asp Pro Asn Thr Thr Asn Leu Arg Pro Thr Thr Tyr Asp Thr Trp Cys
                20                  25                  30

Gly Val Ala His Gly Cys Thr Arg Lys Leu Gly Leu Lys Ile Cys Gly
            35                  40                  45

Phe Leu Gln Arg Thr Asn Ser Leu Glu Glu Lys Ser Arg Leu Val Ser
 50                  55                  60

Ala Phe Arg Glu Arg Gln Ser Ser Lys Asn Leu Leu Ser Cys Glu Asn
 65                  70                  75                  80

Ser Asp Gln Gly Ala Arg Phe Arg Arg Thr Glu Thr Asp Phe Ser Asn
                85                  90                  95

Leu Phe Ala Gln Asp Leu Leu Pro Ala Lys Asn Gly Glu Glu Gln Thr
            100                 105                 110

Ala Gln Phe Leu Leu Glu Val Val Asp Ile Leu Leu Asn Tyr Val Arg
        115                 120                 125

Lys Thr Phe Asp Arg Ser Thr Lys Val Leu Asp Phe His His Pro His
130                 135                 140

Gln Leu Leu Glu Gly Met Glu Gly Phe Asn Leu Glu Leu Ser Asp His
145                 150                 155                 160

Pro Glu Ser Leu Glu Gln Ile Leu Val Asp Cys Arg Asp Thr Leu Lys
                165                 170                 175

Tyr Gly Val Arg Thr Gly His Pro Arg Phe Phe Asn Gln Leu Ser Thr
            180                 185                 190

Gly Leu Asp Ile Ile Gly Leu Ala Gly Glu Trp Leu Thr Ser Thr Ala
        195                 200                 205

Asn Thr Asn Met Phe Thr Tyr Glu Ile Ala Pro Val Phe Val Leu Met
210                 215                 220

Glu Gln Ile Thr Leu Lys Lys Met Arg Lys Ile Val Gly Trp Ser Asn
225                 230                 235                 240

Lys Asp Gly Asp Gly Ile Phe Ser Pro Gly Gly Ala Ile Ser Asn Met
                245                 250                 255

Tyr Ser Ile Met Ala Ala Arg Tyr Lys Tyr Phe Pro Glu Val Lys Thr
            260                 265                 270

Lys Gly Met Ala Ala Val Pro Lys Leu Val Leu Phe Thr Ser Glu His
        275                 280                 285

Ser His Tyr Ser Ile Lys Lys Ala Gly Ala Ala Leu Gly Phe Gly Thr
290                 295                 300

Asp Asn Val Ile Leu Ile Lys Cys Asn Glu Arg Gly Lys Ile Ile Pro
305                 310                 315                 320

Ala Asp Leu Glu Ala Lys Ile Leu Asp Ala Lys Gln Lys Gly Tyr Val
                325                 330                 335

Pro Leu Tyr Val Asn Ala Thr Ala Gly Thr Thr Val Tyr Gly Ala Phe
            340                 345                 350

Asp Pro Ile Gln Glu Ile Ala Asp Ile Cys Glu Lys Tyr Asn Leu Trp
```

```
                    355                 360                 365
Leu His Val Asp Ala Ala Trp Gly Gly Gly Leu Leu Met Ser Arg Lys
        370                 375                 380

His Arg His Lys Leu Ser Gly Ile Glu Arg Ala Asn Ser Val Thr Trp
385                 390                 395                 400

Asn Pro His Lys Met Met Gly Val Leu Leu Gln Cys Ser Ala Ile Leu
                405                 410                 415

Val Lys Glu Lys Gly Ile Leu Gln Gly Cys Asn Gln Met Cys Ala Gly
            420                 425                 430

Tyr Leu Phe Gln Pro Asp Lys Gln Tyr Asp Val Ser Tyr Asp Thr Gly
        435                 440                 445

Asp Lys Ala Ile Gln Cys Gly Arg His Val Asp Ile Phe Lys Phe Trp
    450                 455                 460

Leu Met Trp Lys Ala Lys Gly Thr Val Gly Phe Glu Asn Gln Ile Asn
465                 470                 475                 480

Lys Cys Leu Glu Leu Ala Asp Tyr Leu Tyr Ala Lys Ile Lys Asn Arg
                485                 490                 495

Glu Glu Phe Glu Met Val Phe Asp Gly Glu Pro Glu His Thr Asn Val
            500                 505                 510

Cys Phe Trp Tyr Ile Pro Gln Ser Leu Arg Gly Val Pro Asp Ser Pro
        515                 520                 525

Glu Arg Arg Glu Lys Leu His Arg Val Ala Pro Lys Ile Lys Ala Leu
    530                 535                 540

Met Met Glu Ser Gly Thr Thr Met Val Gly Tyr Gln Pro Gln Gly Asp
545                 550                 555                 560

Lys Ala Asn Phe Phe Arg Met Val Ile Ser Pro Ala Ala Thr Gln
                565                 570                 575

Ser Asp Ile Asp Phe Leu Ile Glu Ile Glu Arg Leu Gly Gln Asp
            580                 585                 590

Leu
```

<210> SEQ ID NO 8
<211> LENGTH: 609
<212> TYPE: DNA
<213> ORGANISM: Unknown Organism
<220> FEATURE:
<223> OTHER INFORMATION: Description of Unknown Organism: N-terminal
      fragment of mouse brain GAD (MBGAD12)
<220> FEATURE:
<221> NAME/KEY: CDS
<222> LOCATION: (1)..(609)

<400> SEQUENCE: 8

```
atg gcg tct tcc act cct tcg cct gca acc tcc tcg aac gcg gga gcg        48
Met Ala Ser Ser Thr Pro Ser Pro Ala Thr Ser Ser Asn Ala Gly Ala
  1               5                  10                  15 gat cct aat act acc aac ctg cgc cct aca acg tat gat act tgg tgt       96
Asp Pro Asn Thr Thr Asn Leu Arg Pro Thr Thr Tyr Asp Thr Trp Cys
                 20                  25                  30 ggc gta gcc cat gga tgc acc aga aaa ctg ggc ctg aag atc tgt ggc      144
Gly Val Ala His Gly Cys Thr Arg Lys Leu Gly Leu Lys Ile Cys Gly
             35                  40                  45 ttc tta caa agg acc aat agc ctg gaa gag aag agt cgt ctt gtg agc      192
Phe Leu Gln Arg Thr Asn Ser Leu Glu Glu Lys Ser Arg Leu Val Ser
         50                  55                  60 gcc ttc agg gag agg cag tcc tcc aag aac ctg ctt tcc tgt gaa aac      240
Ala Phe Arg Glu Arg Gln Ser Ser Lys Asn Leu Leu Ser Cys Glu Asn
     65                  70                  75                  80
```

```
agt gac cag ggt gcc cgc ttc cgg cgc aca gag acc gac ttc tcc aac      288
Ser Asp Gln Gly Ala Arg Phe Arg Arg Thr Glu Thr Asp Phe Ser Asn
                 85                  90                  95 ctg ttt gct caa gat ctg ctt cca gct aag aac ggg gag gag caa act      336
Leu Phe Ala Gln Asp Leu Leu Pro Ala Lys Asn Gly Glu Glu Gln Thr
            100                 105                 110 gcg cag ttc ttg ctg gaa gtg gta gac ata ctc ctc aac tat gtc cgc      384
Ala Gln Phe Leu Leu Glu Val Val Asp Ile Leu Leu Asn Tyr Val Arg
        115                 120                 125 aag aca ttt gat cgc tcc acc aag gtt ctg gat ttc cac cac cca cac      432
Lys Thr Phe Asp Arg Ser Thr Lys Val Leu Asp Phe His His Pro His
    130                 135                 140 cag ttg ctg gaa ggc atg gaa ggc ttt aat ttg gag ctg tct gac cac      480
Gln Leu Leu Glu Gly Met Glu Gly Phe Asn Leu Glu Leu Ser Asp His
145                 150                 155                 160 ccc gag tct ctg gag cag atc ctg gtt gac tgt aga gac acc ctg aag      528
Pro Glu Ser Leu Glu Gln Ile Leu Val Asp Cys Arg Asp Thr Leu Lys
                165                 170                 175 tac ggg gtt cgc aca ggt cac cct cga ttt ttc aac cag ctc tct act      576
Tyr Gly Val Arg Thr Gly His Pro Arg Phe Phe Asn Gln Leu Ser Thr
            180                 185                 190 ggt ttg gat atc att ggt tta gct ggc gaa tgg                          609
Gly Leu Asp Ile Ile Gly Leu Ala Gly Glu Trp
        195                 200

<210> SEQ ID NO 9
<211> LENGTH: 203
<212> TYPE: PRT
<213> ORGANISM: Unknown Organism
<220> FEATURE:
<223> OTHER INFORMATION: Description of Unknown Organism: N-terminal
      fragment of mouse brain GAD (MBGAD12)

<400> SEQUENCE: 9

Met Ala Ser Ser Thr Pro Ser Pro Ala Thr Ser Ser Asn Ala Gly Ala
 1               5                  10                  15

Asp Pro Asn Thr Thr Asn Leu Arg Pro Thr Thr Tyr Asp Thr Trp Cys
            20                  25                  30

Gly Val Ala His Gly Cys Thr Arg Lys Leu Gly Leu Lys Ile Cys Gly
        35                  40                  45

Phe Leu Gln Arg Thr Asn Ser Leu Glu Glu Lys Ser Arg Leu Val Ser
    50                  55                  60

Ala Phe Arg Glu Arg Gln Ser Ser Lys Asn Leu Leu Ser Cys Glu Asn
65                  70                  75                  80

Ser Asp Gln Gly Ala Arg Phe Arg Arg Thr Glu Thr Asp Phe Ser Asn
                85                  90                  95

Leu Phe Ala Gln Asp Leu Leu Pro Ala Lys Asn Gly Glu Glu Gln Thr
            100                 105                 110

Ala Gln Phe Leu Leu Glu Val Val Asp Ile Leu Leu Asn Tyr Val Arg
        115                 120                 125

Lys Thr Phe Asp Arg Ser Thr Lys Val Leu Asp Phe His His Pro His
    130                 135                 140

Gln Leu Leu Glu Gly Met Glu Gly Phe Asn Leu Glu Leu Ser Asp His
145                 150                 155                 160

Pro Glu Ser Leu Glu Gln Ile Leu Val Asp Cys Arg Asp Thr Leu Lys
                165                 170                 175

Tyr Gly Val Arg Thr Gly His Pro Arg Phe Phe Asn Gln Leu Ser Thr
            180                 185                 190
```

Gly Leu Asp Ile Ile Gly Leu Ala Gly Glu Trp
        195                 200

<210> SEQ ID NO 10
<211> LENGTH: 618
<212> TYPE: DNA
<213> ORGANISM: Unknown Organism
<220> FEATURE:
<223> OTHER INFORMATION: Description of Unknown Organism: Mid Region
      Fragment of Mouse Brain GAD (MBGAD34)
<220> FEATURE:
<221> NAME/KEY: CDS
<222> LOCATION: (1)..(618)

<400> SEQUENCE: 10 ggt tta gct ggc gaa tgg ctg aca tcg act gcc aat acc aat atg ttc      48
Gly Leu Ala Gly Glu Trp Leu Thr Ser Thr Ala Asn Thr Asn Met Phe
 1               5                  10                  15 aca tat gaa att gca ccc gtg ttt gtt ctc atg gaa cag att act ctt      96
Thr Tyr Glu Ile Ala Pro Val Phe Val Leu Met Glu Gln Ile Thr Leu
             20                  25                  30 aag aag atg aga aag atc gtt gga tgg tca aat aaa gat ggt gat ggg     144
Lys Lys Met Arg Lys Ile Val Gly Trp Ser Asn Lys Asp Gly Asp Gly
         35                  40                  45 ata ttt tct cct ggg gga gcc ata tcc aat atg tac agc atc atg gct     192
Ile Phe Ser Pro Gly Gly Ala Ile Ser Asn Met Tyr Ser Ile Met Ala
     50                  55                  60 gct cgt tac aag tac ttc cca gaa gtg aag aca aaa ggc atg gcg gct     240
Ala Arg Tyr Lys Tyr Phe Pro Glu Val Lys Thr Lys Gly Met Ala Ala
 65                  70                  75                  80 gtg ccc aaa ctg gtc ctc ttc acc tca gaa cac agt cac tat tcc ata     288
Val Pro Lys Leu Val Leu Phe Thr Ser Glu His Ser His Tyr Ser Ile
                 85                  90                  95 aag aaa gcc ggg gct gcg ctt ggc ttt gga acc gac aat gtg att ttg     336
Lys Lys Ala Gly Ala Ala Leu Gly Phe Gly Thr Asp Asn Val Ile Leu
            100                 105                 110 ata aag tgc aat gaa agg ggg aag ata att ccg gct gat tta gag gca     384
Ile Lys Cys Asn Glu Arg Gly Lys Ile Ile Pro Ala Asp Leu Glu Ala
        115                 120                 125 aaa att ctt gat gcc aaa caa aag ggc tat gtt ccc ctt tat gtc aat     432
Lys Ile Leu Asp Ala Lys Gln Lys Gly Tyr Val Pro Leu Tyr Val Asn
    130                 135                 140 gca acc gca ggc acg act gtt tac gga gca ttc gat cca atc cag gaa     480
Ala Thr Ala Gly Thr Thr Val Tyr Gly Ala Phe Asp Pro Ile Gln Glu
145                 150                 155                 160 att gcg gac ata tgt gag aaa tac aac ctt tgg ctg cat gtg gat gct     528
Ile Ala Asp Ile Cys Glu Lys Tyr Asn Leu Trp Leu His Val Asp Ala
                165                 170                 175 gcc tgg ggt ggt gga ctg ctc atg tcc cgg aag cac cgc cac aaa ctc     576
Ala Trp Gly Gly Gly Leu Leu Met Ser Arg Lys His Arg His Lys Leu
            180                 185                 190 agc ggc ata gaa agg gcc aat tca gtc acc tgg aac cct cac                 618
Ser Gly Ile Glu Arg Ala Asn Ser Val Thr Trp Asn Pro His
        195                 200                 205

<210> SEQ ID NO 11
<211> LENGTH: 206
<212> TYPE: PRT
<213> ORGANISM: Unknown Organism
<220> FEATURE:
<223> OTHER INFORMATION: Description of Unknown Organism: Mid Region
      Fragment of Mouse Brain GAD (MBGAD34)

<400> SEQUENCE: 11

Gly Leu Ala Gly Glu Trp Leu Thr Ser Thr Ala Asn Thr Asn Met Phe
  1               5                  10                  15

Thr Tyr Glu Ile Ala Pro Val Phe Val Leu Met Glu Gln Ile Thr Leu
             20                  25                  30

Lys Lys Met Arg Lys Ile Val Gly Trp Ser Asn Lys Asp Gly Asp Gly
         35                  40                  45

Ile Phe Ser Pro Gly Gly Ala Ile Ser Asn Met Tyr Ser Ile Met Ala
     50                  55                  60

Ala Arg Tyr Lys Tyr Phe Pro Glu Val Lys Thr Lys Gly Met Ala Ala
 65                  70                  75                  80

Val Pro Lys Leu Val Leu Phe Thr Ser Glu His Ser His Tyr Ser Ile
             85                  90                  95

Lys Lys Ala Gly Ala Ala Leu Gly Phe Gly Thr Asp Asn Val Ile Leu
            100                 105                 110

Ile Lys Cys Asn Glu Arg Gly Lys Ile Ile Pro Ala Asp Leu Glu Ala
            115                 120                 125

Lys Ile Leu Asp Ala Lys Gln Lys Gly Tyr Val Pro Leu Tyr Val Asn
        130                 135                 140

Ala Thr Ala Gly Thr Thr Val Tyr Gly Ala Phe Asp Pro Ile Gln Glu
145                 150                 155                 160

Ile Ala Asp Ile Cys Glu Lys Tyr Asn Leu Trp Leu His Val Asp Ala
                165                 170                 175

Ala Trp Gly Gly Gly Leu Leu Met Ser Arg Lys His Arg His Lys Leu
                180                 185                 190

Ser Gly Ile Glu Arg Ala Asn Ser Val Thr Trp Asn Pro His
            195                 200                 205

<210> SEQ ID NO 12
<211> LENGTH: 612
<212> TYPE: DNA
<213> ORGANISM: Unknown Organism
<220> FEATURE:
<223> OTHER INFORMATION: Description of Unknown Organism: C-terminal
      fragment of Mouse Brain GAD (MBGAD56)
<220> FEATURE:
<221> NAME/KEY: CDS
<222> LOCATION: (1)..(609)

<400> SEQUENCE: 12

```
ggc ata gaa agg gcc aat tca gtc acc tgg aac cct cac aag atg atg      48
Gly Ile Glu Arg Ala Asn Ser Val Thr Trp Asn Pro His Lys Met Met
  1               5                  10                  15 ggc gtg ctg ctc cag tgc tct gcc att ctg gtc aag gaa aag ggt ata      96
Gly Val Leu Leu Gln Cys Ser Ala Ile Leu Val Lys Glu Lys Gly Ile
             20                  25                  30 ctc caa gga tgc aac cag atg tgt gca ggc tac ctc ttc cag cca gac     144
Leu Gln Gly Cys Asn Gln Met Cys Ala Gly Tyr Leu Phe Gln Pro Asp
         35                  40                  45 aag cag tat gac gtc tcc tat gac acc ggg gac aag gcg att cag tgt     192
Lys Gln Tyr Asp Val Ser Tyr Asp Thr Gly Asp Lys Ala Ile Gln Cys
     50                  55                  60 ggc cgc cat gtg gac atc ttc aag ttc tgg ctg atg tgg aaa gca aag     240
Gly Arg His Val Asp Ile Phe Lys Phe Trp Leu Met Trp Lys Ala Lys
 65                  70                  75                  80 ggc acc gtg gga ttt gaa aac cag atc aac aaa tgc ctg gag ctg gct     288
Gly Thr Val Gly Phe Glu Asn Gln Ile Asn Lys Cys Leu Glu Leu Ala
             85                  90                  95
```

```
gat tac ctc tac gcc aag att aaa aac aga gaa gag ttt gag atg gtt    336
Asp Tyr Leu Tyr Ala Lys Ile Lys Asn Arg Glu Glu Phe Glu Met Val
            100                 105                 110 ttc gat ggt gag cct gag cac aca aat gtc tgt ttc tgg tac att cca    384
Phe Asp Gly Glu Pro Glu His Thr Asn Val Cys Phe Trp Tyr Ile Pro
        115                 120                 125 caa agc ctt aga ggg gtt cca gat agc cct gag cga cga gaa aag cta    432
Gln Ser Leu Arg Gly Val Pro Asp Ser Pro Glu Arg Arg Glu Lys Leu
    130                 135                 140 cac agg gtg gct ccc aag atc aaa gct ctg atg atg gag tca gga aca    480
His Arg Val Ala Pro Lys Ile Lys Ala Leu Met Met Glu Ser Gly Thr
145                 150                 155                 160 acc atg gtc ggc tac cag cct caa ggg gac aag gcc aac ttc ttc cgg    528
Thr Met Val Gly Tyr Gln Pro Gln Gly Asp Lys Ala Asn Phe Phe Arg
                165                 170                 175 atg gtc atc tct aac cca gcc gcc acc cag tct gac atc gat ttc ctc    576
Met Val Ile Ser Asn Pro Ala Ala Thr Gln Ser Asp Ile Asp Phe Leu
            180                 185                 190 att gag gag ata gag agg ttg ggc cag gat ctg taa                    612
Ile Glu Glu Ile Glu Arg Leu Gly Gln Asp Leu
        195                 200

<210> SEQ ID NO 13
<211> LENGTH: 203
<212> TYPE: PRT
<213> ORGANISM: Unknown Organism
<220> FEATURE:
<223> OTHER INFORMATION: Description of Unknown Organism: C-terminal
      fragment of Mouse Brain GAD (MBGAD56)

<400> SEQUENCE: 13

Gly Ile Glu Arg Ala Asn Ser Val Thr Trp Asn Pro His Lys Met Met
 1               5                  10                  15

Val Leu Leu Gln Cys Ser Ala Ile Leu Val Lys Glu Lys Gly Ile
            20                  25                  30

Leu Gln Gly Cys Asn Gln Met Cys Ala Gly Tyr Leu Phe Gln Pro Asp
        35                  40                  45

Lys Gln Tyr Asp Val Ser Tyr Asp Thr Gly Asp Lys Ala Ile Gln Cys
    50                  55                  60

Gly Arg His Val Asp Ile Phe Lys Phe Trp Leu Met Trp Lys Ala Lys
65                  70                  75                  80

Gly Thr Val Gly Phe Glu Asn Gln Ile Asn Lys Cys Leu Glu Leu Ala
                85                  90                  95

Asp Tyr Leu Tyr Ala Lys Ile Lys Asn Arg Glu Glu Phe Glu Met Val
            100                 105                 110

Phe Asp Gly Glu Pro Glu His Thr Asn Val Cys Phe Trp Tyr Ile Pro
        115                 120                 125

Gln Ser Leu Arg Gly Val Pro Asp Ser Pro Glu Arg Arg Glu Lys Leu
    130                 135                 140

His Arg Val Ala Pro Lys Ile Lys Ala Leu Met Met Glu Ser Gly Thr
145                 150                 155                 160

Thr Met Val Gly Tyr Gln Pro Gln Gly Asp Lys Ala Asn Phe Phe Arg
                165                 170                 175

Met Val Ile Ser Asn Pro Ala Ala Thr Gln Ser Asp Ile Asp Phe Leu
            180                 185                 190

Ile Glu Glu Ile Glu Arg Leu Gly Gln Asp Leu
        195                 200
```

-continued

<210> SEQ ID NO 14
<211> LENGTH: 1785
<212> TYPE: DNA
<213> ORGANISM: Unknown Organism
<220> FEATURE:
<223> OTHER INFORMATION: Description of Unknown Organism: Full Length
      Nucleotide Sequence of Human Brain GAD (HBGAD-FL)
<220> FEATURE:
<221> NAME/KEY: CDS
<222> LOCATION: (1)..(1782)

<400> SEQUENCE: 14

```
atg gcg tct tcg acc cca tct tcg tcc gca acc tcc tcg aac gcg gga         48
Met Ala Ser Ser Thr Pro Ser Ser Ser Ala Thr Ser Ser Asn Ala Gly
 1               5                  10                  15 gcg gac ccc aat acc act aac ctg cgc ccc aca acg tac gat acc tgg         96
Ala Asp Pro Asn Thr Thr Asn Leu Arg Pro Thr Thr Tyr Asp Thr Trp
             20                  25                  30 tgc ggc gtg gcc cat gga tgc acc aga aaa ctg ggc ctc aag atc tgc        144
Cys Gly Val Ala His Gly Cys Thr Arg Lys Leu Gly Leu Lys Ile Cys
         35                  40                  45 ggc ttc ttg caa agg acc aac agc ctg gaa gag aag agt cgc ctt gtg        192
Gly Phe Leu Gln Arg Thr Asn Ser Leu Glu Glu Lys Ser Arg Leu Val
 50                  55                  60 agt gcc ttc aag gag agg caa tcc tcc aag aac ctg ctt tcc tgt gaa        240
Ser Ala Phe Lys Glu Arg Gln Ser Ser Lys Asn Leu Leu Ser Cys Glu
 65                  70                  75                  80 aac agc gac cgg gat gcc cgc ttc cgg cgc aca gag act gac ttc tct        288
Asn Ser Asp Arg Asp Ala Arg Phe Arg Arg Thr Glu Thr Asp Phe Ser
                 85                  90                  95 aat ctg ttt gct aga gat ctg ctt ccg gct aag aac ggt gag gag caa        336
Asn Leu Phe Ala Arg Asp Leu Leu Pro Ala Lys Asn Gly Glu Glu Gln
            100                 105                 110 acc gtg caa ttc ctc ctg gaa gtg gtg gac ata ctc ctc aac tat gtc        384
Thr Val Gln Phe Leu Leu Glu Val Val Asp Ile Leu Leu Asn Tyr Val
        115                 120                 125 cgc aag aca ttt gat cgc tcc acc aag gtg ctg gac ttt cat cac cca        432
Arg Lys Thr Phe Asp Arg Ser Thr Lys Val Leu Asp Phe His His Pro
    130                 135                 140 cac cag ttg ctg gaa ggc atg gag ggc ttc aac ttg gag ctc tct gac        480
His Gln Leu Leu Glu Gly Met Glu Gly Phe Asn Leu Glu Leu Ser Asp
145                 150                 155                 160 cac ccc gag tcc ctg gag cag atc ctg gtc gac tgc aga gac acc ttg        528
His Pro Glu Ser Leu Glu Gln Ile Leu Val Asp Cys Arg Asp Thr Leu
                165                 170                 175 aag tat ggg gtt cgc aca ggt cat cct cga ttt ttc aac cag ctc tcc        576
Lys Tyr Gly Val Arg Thr Gly His Pro Arg Phe Phe Asn Gln Leu Ser
            180                 185                 190 act gga ttg gat att att ggc cta gct gga gaa tgg ctg aca tca acg        624
Thr Gly Leu Asp Ile Ile Gly Leu Ala Gly Glu Trp Leu Thr Ser Thr
        195                 200                 205 gcc aat acc aac atg ttc aca tat gaa att gca cca gtg ttt gtc ctc        672
Ala Asn Thr Asn Met Phe Thr Tyr Glu Ile Ala Pro Val Phe Val Leu
    210                 215                 220 atg gaa caa ata aca ctt aag aag atg aga gag ata gtt gga tgg tca        720
Met Glu Gln Ile Thr Leu Lys Lys Met Arg Glu Ile Val Gly Trp Ser
225                 230                 235                 240 agt aaa gat ggt gat ggg ata ttt tct cct ggg ggc gcc ata tcc aac        768
Ser Lys Asp Gly Asp Gly Ile Phe Ser Pro Gly Gly Ala Ile Ser Asn
                245                 250                 255 atg tac agc atc atg gct gct cgc tac aag tac ttc ccg gaa gtt aag        816
Met Tyr Ser Ile Met Ala Ala Arg Tyr Lys Tyr Phe Pro Glu Val Lys
```

-continued

```
                260                      265                      270
aca aag ggc atg gcg gct gtg cct aaa ctg gtc ctc ttc acc tca gaa         864
Thr Lys Gly Met Ala Ala Val Pro Lys Leu Val Leu Phe Thr Ser Glu
            275                      280                      285 cag agt cac tat tcc ata aag aaa gct ggg gct gca ctt ggc ttt gga         912
Gln Ser His Tyr Ser Ile Lys Lys Ala Gly Ala Ala Leu Gly Phe Gly
        290                      295                      300 act gac aat gtg att ttg ata aag tgc aat gaa agg ggg aaa ata att         960
Thr Asp Asn Val Ile Leu Ile Lys Cys Asn Glu Arg Gly Lys Ile Ile
305                      310                      315                      320 cca gct gat ttt gag gca aaa att ctt gaa gcc aaa cag aag gga tat        1008
Pro Ala Asp Phe Glu Ala Lys Ile Leu Glu Ala Lys Gln Lys Gly Tyr
                325                      330                      335 gtt ccc ttt tat gtc aat gca act gct ggc acg act gtt tat gga gct        1056
Val Pro Phe Tyr Val Asn Ala Thr Ala Gly Thr Thr Val Tyr Gly Ala
            340                      345                      350 ttt gat ccg ata caa gag att gca gat ata tgt gag aaa tat aac ctt        1104
Phe Asp Pro Ile Gln Glu Ile Ala Asp Ile Cys Glu Lys Tyr Asn Leu
        355                      360                      365 tgg ttg cat gtc gat gct gcc tgg gga ggt ggg ctg ctc atg tcc agg        1152
Trp Leu His Val Asp Ala Ala Trp Gly Gly Gly Leu Leu Met Ser Arg
    370                      375                      380 aag cac cgc cat aaa ctc aac ggc ata gaa agg gcc aac tca gtc acc        1200
Lys His Arg His Lys Leu Asn Gly Ile Glu Arg Ala Asn Ser Val Thr
385                      390                      395                      400 tgg aac cct cac aag atg atg ggc gtg ctg ttg cag tgc tct gcc att        1248
Trp Asn Pro His Lys Met Met Gly Val Leu Leu Gln Cys Ser Ala Ile
                405                      410                      415 ctc gtc aag gaa aag ggt ata ctc caa gga tgc aac cag atg tgt gca        1296
Leu Val Lys Glu Lys Gly Ile Leu Gln Gly Cys Asn Gln Met Cys Ala
            420                      425                      430 gga tac ctc ctc cag cca gac aag cag tat gat gtc tcc tac gac acc        1344
Gly Tyr Leu Leu Gln Pro Asp Lys Gln Tyr Asp Val Ser Tyr Asp Thr
        435                      440                      445 ggg gac aag gca att cag tgt ggc cgc cac gtg gat atc ttc aag ttc        1392
Gly Asp Lys Ala Ile Gln Cys Gly Arg His Val Asp Ile Phe Lys Phe
    450                      455                      460 tgg ctg atg tgg aaa gca aag ggc aca gtg gga ttt gaa aac cag atc        1440
Trp Leu Met Trp Lys Ala Lys Gly Thr Val Gly Phe Glu Asn Gln Ile
465                      470                      475                      480 aac aaa tgc ctg gaa ctg gct gaa tac ctc tat gcc aag att aaa aac        1488
Asn Lys Cys Leu Glu Leu Ala Glu Tyr Leu Tyr Ala Lys Ile Lys Asn
                485                      490                      495 aga gaa gaa ttt gag atg gtt ttc aat ggc gag cct gag cac aca aac        1536
Arg Glu Glu Phe Glu Met Val Phe Asn Gly Glu Pro Glu His Thr Asn
            500                      505                      510 gtc tgt ttt tgg tat att cca caa agc ctc agg ggt gtg cca gac agc        1584
Val Cys Phe Trp Tyr Ile Pro Gln Ser Leu Arg Gly Val Pro Asp Ser
        515                      520                      525 cct caa cga cgg gaa aag cta cac aag gtg gct cca aaa atc aaa gcc        1632
Pro Gln Arg Arg Glu Lys Leu His Lys Val Ala Pro Lys Ile Lys Ala
    530                      535                      540 ctg atg atg gag tca ggt acg acc atg gtt ggc tac cag ccc caa ggg        1680
Leu Met Met Glu Ser Gly Thr Thr Met Val Gly Tyr Gln Pro Gln Gly
545                      550                      555                      560 gac aag gcc aac ttc ttc cgg atg gtc atc tcc aac cca gcc gct acc        1728
Asp Lys Ala Asn Phe Phe Arg Met Val Ile Ser Asn Pro Ala Ala Thr
                565                      570                      575 cag tct gac att gac ttc ctc att gag gag ata gaa aga ctg ggc cag        1776
```

```
Gln Ser Asp Ile Asp Phe Leu Ile Glu Glu Ile Glu Arg Leu Gly Gln
            580                 585                 590 gat ctg taa                                                          1785
Asp Leu <210> SEQ ID NO 15
<211> LENGTH: 594
<212> TYPE: PRT
<213> ORGANISM: Unknown Organism
<220> FEATURE:
<223> OTHER INFORMATION: Description of Unknown Organism: Human Brain
      GAD (HBGAD-FL)

<400> SEQUENCE: 15

Met Ala Ser Ser Thr Pro Ser Ser Ala Thr Ser Ser Asn Ala Gly
  1               5                  10                  15

Ala Asp Pro Asn Thr Thr Asn Leu Arg Pro Thr Thr Tyr Asp Thr Trp
                 20                  25                  30

Cys Gly Val Ala His Gly Cys Thr Arg Lys Leu Gly Leu Lys Ile Cys
             35                  40                  45

Gly Phe Leu Gln Arg Thr Asn Ser Leu Glu Glu Lys Ser Arg Leu Val
 50                  55                  60

Ser Ala Phe Lys Glu Arg Gln Ser Ser Lys Asn Leu Leu Ser Cys Glu
 65                  70                  75                  80

Asn Ser Asp Arg Asp Ala Arg Phe Arg Arg Thr Glu Thr Asp Phe Ser
                 85                  90                  95

Asn Leu Phe Ala Arg Asp Leu Leu Pro Ala Lys Asn Gly Glu Glu Gln
                100                 105                 110

Thr Val Gln Phe Leu Leu Glu Val Val Asp Ile Leu Leu Asn Tyr Val
            115                 120                 125

Arg Lys Thr Phe Asp Arg Ser Thr Lys Val Leu Asp Phe His His Pro
130                 135                 140

His Gln Leu Leu Glu Gly Met Glu Gly Phe Asn Leu Glu Leu Ser Asp
145                 150                 155                 160

His Pro Glu Ser Leu Glu Gln Ile Leu Val Asp Cys Arg Asp Thr Leu
                165                 170                 175

Lys Tyr Gly Val Arg Thr Gly His Pro Arg Phe Phe Asn Gln Leu Ser
            180                 185                 190

Thr Gly Leu Asp Ile Ile Gly Leu Ala Gly Glu Trp Leu Thr Ser Thr
            195                 200                 205

Ala Asn Thr Asn Met Phe Thr Tyr Glu Ile Ala Pro Val Phe Val Leu
210                 215                 220

Met Glu Gln Ile Thr Leu Lys Lys Met Arg Glu Ile Val Gly Trp Ser
225                 230                 235                 240

Ser Lys Asp Gly Asp Gly Ile Phe Ser Pro Gly Gly Ala Ile Ser Asn
                245                 250                 255

Met Tyr Ser Ile Met Ala Ala Arg Tyr Lys Tyr Phe Pro Glu Val Lys
            260                 265                 270

Thr Lys Gly Met Ala Ala Val Pro Lys Leu Val Leu Phe Thr Ser Glu
            275                 280                 285

Gln Ser His Tyr Ser Ile Lys Lys Ala Gly Ala Ala Leu Gly Phe Gly
            290                 295                 300

Thr Asp Asn Val Ile Leu Ile Lys Cys Asn Glu Arg Gly Lys Ile Ile
305                 310                 315                 320

Pro Ala Asp Phe Glu Ala Lys Ile Leu Glu Ala Lys Gln Lys Gly Tyr
                325                 330                 335
```

-continued

```
Val Pro Phe Tyr Val Asn Ala Thr Ala Gly Thr Thr Val Tyr Gly Ala
            340                 345                 350

Phe Asp Pro Ile Gln Glu Ile Ala Asp Ile Cys Glu Lys Tyr Asn Leu
            355                 360                 365

Trp Leu His Val Asp Ala Ala Trp Gly Gly Gly Leu Leu Met Ser Arg
        370                 375                 380

Lys His Arg His Lys Leu Asn Gly Ile Glu Arg Ala Asn Ser Val Thr
385                 390                 395                 400

Trp Asn Pro His Lys Met Met Gly Val Leu Leu Gln Cys Ser Ala Ile
                405                 410                 415

Leu Val Lys Glu Lys Gly Ile Leu Gln Gly Cys Asn Gln Met Cys Ala
            420                 425                 430

Gly Tyr Leu Leu Gln Pro Asp Lys Gln Tyr Asp Val Ser Tyr Asp Thr
        435                 440                 445

Gly Asp Lys Ala Ile Gln Cys Gly Arg His Val Asp Ile Phe Lys Phe
    450                 455                 460

Trp Leu Met Trp Lys Ala Lys Gly Thr Val Gly Phe Glu Asn Gln Ile
465                 470                 475                 480

Asn Lys Cys Leu Glu Leu Ala Glu Tyr Leu Tyr Ala Lys Ile Lys Asn
                485                 490                 495

Arg Glu Glu Phe Glu Met Val Phe Asn Gly Glu Pro Glu His Thr Asn
            500                 505                 510

Val Cys Phe Trp Tyr Ile Pro Gln Ser Leu Arg Gly Val Pro Asp Ser
        515                 520                 525

Pro Gln Arg Arg Glu Lys Leu His Lys Val Ala Pro Lys Ile Lys Ala
    530                 535                 540

Leu Met Met Glu Ser Gly Thr Thr Met Val Gly Tyr Gln Pro Gln Gly
545                 550                 555                 560

Asp Lys Ala Asn Phe Phe Arg Met Val Ile Ser Asn Pro Ala Ala Thr
                565                 570                 575

Gln Ser Asp Ile Asp Phe Leu Ile Glu Glu Ile Glu Arg Leu Gly Gln
            580                 585                 590

Asp Leu
```

<210> SEQ ID NO 16
<211> LENGTH: 750
<212> TYPE: DNA
<213> ORGANISM: Unknown Organism
<220> FEATURE:
<223> OTHER INFORMATION: Description of Unknown Organism:N-terminal
    Fragment of Human Brain GAD (HBGAD17)
<220> FEATURE:
<221> NAME/KEY: CDS
<222> LOCATION: (1)..(750)

<400> SEQUENCE: 16

```
atg gcg tct tcg acc cca tct tcg tcc gca acc tcc tcg aac gcg gga        48
Met Ala Ser Ser Thr Pro Ser Ser Ser Ala Thr Ser Ser Asn Ala Gly
  1               5                  10                  15 gcg gac ccc aat acc act aac ctg cgc ccc aca acg tac gat acc tgg        96
Ala Asp Pro Asn Thr Thr Asn Leu Arg Pro Thr Thr Tyr Asp Thr Trp
             20                  25                  30 tgc ggc gtg gcc cat gga tgc acc aga aaa ctg ggg ctc aag atc tgc       144
Cys Gly Val Ala His Gly Cys Thr Arg Lys Leu Gly Leu Lys Ile Cys
         35                  40                  45 ggc ttc ttg caa agg acc aac agc ctg gaa gag aag agt cgc ctt gtg       192
Gly Phe Leu Gln Arg Thr Asn Ser Leu Glu Glu Lys Ser Arg Leu Val
     50                  55                  60
```

```
                 50                    55                    60
agt gcc ttc aag gag agg caa tcc tcc aag aac ctg ctt tcc tgt gaa        240
Ser Ala Phe Lys Glu Arg Gln Ser Ser Lys Asn Leu Leu Ser Cys Glu
65              70                      75                      80 aac agc gac cgg gat gcc cgc ttc cgg cgc aca gag act gac ttc tct        288
Asn Ser Asp Arg Asp Ala Arg Phe Arg Arg Thr Glu Thr Asp Phe Ser
                    85                      90                      95 aat ctg ttt gct aga gat ctg ctt ccg gct aag aac ggt gag gag caa        336
Asn Leu Phe Ala Arg Asp Leu Leu Pro Ala Lys Asn Gly Glu Glu Gln
                100                     105                     110 acc gtg caa ttc ctc ctg gaa gtg gtg gac ata ctc ctc aac tat gtc        384
Thr Val Gln Phe Leu Leu Glu Val Val Asp Ile Leu Leu Asn Tyr Val
            115                     120                     125 cgc aag aca ttt gat cgc tcc acc aag gtg ctg gac ttt cat cac cca        432
Arg Lys Thr Phe Asp Arg Ser Thr Lys Val Leu Asp Phe His His Pro
        130                     135                     140 cac cag ttg ctg gaa ggc atg gag ggc ttc aac ttg gag ctc tct gac        480
His Gln Leu Leu Glu Gly Met Glu Gly Phe Asn Leu Glu Leu Ser Asp
145                     150                     155                     160 cac ccc gag tcc ctg gag cag atc ctg gtc gac tgc aga gac acc ttg        528
His Pro Glu Ser Leu Glu Gln Ile Leu Val Asp Cys Arg Asp Thr Leu
                    165                     170                     175 aag tat ggg gtt cgc aca ggt cat cct cga ttt ttc aac cag ctc tcc        576
Lys Tyr Gly Val Arg Thr Gly His Pro Arg Phe Phe Asn Gln Leu Ser
                180                     185                     190 act gga ttg gat att att ggc cta gct gga gaa tgg ctg aca tca acg        624
Thr Gly Leu Asp Ile Ile Gly Leu Ala Gly Glu Trp Leu Thr Ser Thr
            195                     200                     205 gcc aat acc aac atg ttc aca tat gaa att gca cca gtg ttt gtc ctc        672
Ala Asn Thr Asn Met Phe Thr Tyr Glu Ile Ala Pro Val Phe Val Leu
        210                     215                     220 atg gaa caa ata aca ctt aag aag atg aga gag ata gtt gga tgg tca        720
Met Glu Gln Ile Thr Leu Lys Lys Met Arg Glu Ile Val Gly Trp Ser
225                     230                     235                     240 agt aaa gat ggt gat ggg ata ttt tct cct                                750
Ser Lys Asp Gly Asp Gly Ile Phe Ser Pro
                    245                     250
```

<210> SEQ ID NO 17
<211> LENGTH: 250
<212> TYPE: PRT
<213> ORGANISM: Unknown Organism
<220> FEATURE:
<223> OTHER INFORMATION: Description of Unknown Organism:N-terminal
      Fragment of Human Brain GAD (HBGAD17)

<400> SEQUENCE: 17

```
Met Ala Ser Ser Thr Pro Ser Ser Ser Ala Thr Ser Ser Asn Ala Gly
1               5                   10                  15

Ala Asp Pro Asn Thr Thr Asn Leu Arg Pro Thr Thr Tyr Asp Thr Trp
            20                  25                  30

Cys Gly Val Ala His Gly Cys Thr Arg Lys Leu Gly Leu Lys Ile Cys
        35                  40                  45

Gly Phe Leu Gln Arg Thr Asn Ser Leu Glu Glu Lys Ser Arg Leu Val
    50                  55                  60

Ser Ala Phe Lys Glu Arg Gln Ser Ser Lys Asn Leu Leu Ser Cys Glu
65              70                  75                  80

Asn Ser Asp Arg Asp Ala Arg Phe Arg Arg Thr Glu Thr Asp Phe Ser
                85                  90                  95
```

```
Asn Leu Phe Ala Arg Asp Leu Leu Pro Ala Lys Asn Gly Glu Glu Gln
            100                 105                 110

Thr Val Gln Phe Leu Leu Glu Val Val Asp Ile Leu Leu Asn Tyr Val
        115                 120                 125

Arg Lys Thr Phe Asp Arg Ser Thr Lys Val Leu Asp Phe His His Pro
    130                 135                 140

His Gln Leu Leu Glu Gly Met Glu Gly Phe Asn Leu Glu Leu Ser Asp
145                 150                 155                 160

His Pro Glu Ser Leu Glu Gln Ile Leu Val Asp Cys Arg Asp Thr Leu
                165                 170                 175

Lys Tyr Gly Val Arg Thr Gly His Pro Arg Phe Phe Asn Gln Leu Ser
            180                 185                 190

Thr Gly Leu Asp Ile Ile Gly Leu Ala Gly Glu Trp Leu Thr Ser Thr
        195                 200                 205

Ala Asn Thr Asn Met Phe Thr Tyr Glu Ile Ala Pro Val Phe Val Leu
    210                 215                 220

Met Glu Gln Ile Thr Leu Lys Lys Met Arg Glu Ile Val Gly Trp Ser
225                 230                 235                 240

Ser Lys Asp Gly Asp Gly Ile Phe Ser Pro
                245                 250

<210> SEQ ID NO 18
<211> LENGTH: 591
<212> TYPE: DNA
<213> ORGANISM: Unknown Organism
<220> FEATURE:
<223> OTHER INFORMATION: Description of Unknown Organism:Mid Region
      Fragment of Human Brain GAD (HBGAD14)
<220> FEATURE:
<221> NAME/KEY: CDS
<222> LOCATION: (1)..(591)

<400> SEQUENCE: 18 acg gcc aat acc aac atg ttc aca tat gaa att gca cca gtg ttt gtc      48
Thr Ala Asn Thr Asn Met Phe Thr Tyr Glu Ile Ala Pro Val Phe Val
  1               5                  10                  15 ctc atg gaa caa ata aca ctt aag aag atg aga gag ata gtt gga tgg      96
Leu Met Glu Gln Ile Thr Leu Lys Lys Met Arg Glu Ile Val Gly Trp
             20                  25                  30 tca agt aaa gat ggt gat ggg ata ttt tct cct ggg ggc gcc ata tcc     144
Ser Ser Lys Asp Gly Asp Gly Ile Phe Ser Pro Gly Gly Ala Ile Ser
         35                  40                  45 aac atg tac agc atc atg gct gct cgc tac aag tac ttc ccg gaa gtt     192
Asn Met Tyr Ser Ile Met Ala Ala Arg Tyr Lys Tyr Phe Pro Glu Val
     50                  55                  60 aag aca aag ggc atg gcg gct gtg cct aaa ctg gtc ctc ttc acc tca     240
Lys Thr Lys Gly Met Ala Ala Val Pro Lys Leu Val Leu Phe Thr Ser
 65                  70                  75                  80 gaa cag agt cac tat tcc ata aag aaa gct ggg gct gca ctt ggc ttt     288
Glu Gln Ser His Tyr Ser Ile Lys Lys Ala Gly Ala Ala Leu Gly Phe
                 85                  90                  95 gga act gac aat gtg att ttg ata aag tgc aat gaa agg ggg aaa ata     336
Gly Thr Asp Asn Val Ile Leu Ile Lys Cys Asn Glu Arg Gly Lys Ile
            100                 105                 110 att cca gct gat ttt gag gca aaa att ctt gaa gcc aaa cag aag gga     384
Ile Pro Ala Asp Phe Glu Ala Lys Ile Leu Glu Ala Lys Gln Lys Gly
        115                 120                 125 tat gtt ccc ttt tat gtc aat gca act gct ggc acg act gtt tat gga     432
Tyr Val Pro Phe Tyr Val Asn Ala Thr Ala Gly Thr Thr Val Tyr Gly
    130                 135                 140
```

-continued

```
gct ttt gat ccg ata caa gag att gca gat ata tgt gag aaa tat aac        480
Ala Phe Asp Pro Ile Gln Glu Ile Ala Asp Ile Cys Glu Lys Tyr Asn
145                 150                 155                 160 ctt tgg ttg cat gtc gat gct gcc tgg gga ggt ggg ctg ctc atg tcc        528
Leu Trp Leu His Val Asp Ala Ala Trp Gly Gly Gly Leu Leu Met Ser
                165                 170                 175 agg aag cac cgc cat aaa ctc aac ggc ata gaa agg gcc aac tca gtc        576
Arg Lys His Arg His Lys Leu Asn Gly Ile Glu Arg Ala Asn Ser Val
            180                 185                 190 acc tgg aac cct cac                                                    591
Thr Trp Asn Pro His
        195
```

<210> SEQ ID NO 19
<211> LENGTH: 197
<212> TYPE: PRT
<213> ORGANISM: Unknown Organism
<220> FEATURE:
<223> OTHER INFORMATION: Description of Unknown Organism:Mid Region
    Fragment of Human Brain GAD (HBGAD14)

<400> SEQUENCE: 19

```
Thr Ala Asn Thr Asn Met Phe Thr Tyr Glu Ile Ala Pro Val Phe Val
  1               5                  10                  15

Leu Met Glu Gln Ile Thr Leu Lys Lys Met Arg Glu Ile Val Gly Trp
             20                  25                  30

Ser Ser Lys Asp Gly Asp Gly Ile Phe Ser Pro Gly Gly Ala Ile Ser
         35                  40                  45

Asn Met Tyr Ser Ile Met Ala Ala Arg Tyr Lys Tyr Phe Pro Glu Val
     50                  55                  60

Lys Thr Lys Gly Met Ala Ala Val Pro Lys Leu Val Leu Phe Thr Ser
 65                  70                  75                  80

Glu Gln Ser His Tyr Ser Ile Lys Lys Ala Gly Ala Ala Leu Gly Phe
                 85                  90                  95

Gly Thr Asp Asn Val Ile Leu Ile Lys Cys Asn Glu Arg Gly Lys Ile
            100                 105                 110

Ile Pro Ala Asp Phe Glu Ala Lys Ile Leu Glu Ala Lys Gln Lys Gly
        115                 120                 125

Tyr Val Pro Phe Tyr Val Asn Ala Thr Ala Gly Thr Thr Val Tyr Gly
    130                 135                 140

Ala Phe Asp Pro Ile Gln Glu Ile Ala Asp Ile Cys Glu Lys Tyr Asn
145                 150                 155                 160

Leu Trp Leu His Val Asp Ala Ala Trp Gly Gly Gly Leu Leu Met Ser
                165                 170                 175

Arg Lys His Arg His Lys Leu Asn Gly Ile Glu Arg Ala Asn Ser Val
            180                 185                 190

Thr Trp Asn Pro His
        195
```

<210> SEQ ID NO 20
<211> LENGTH: 612
<212> TYPE: DNA
<213> ORGANISM: Unknown Organism
<220> FEATURE:
<223> OTHER INFORMATION: Description of Unknown Organism: C-terminal
    Fragment of Human Brain GAD (HBGAD65)
<220> FEATURE:
<221> NAME/KEY: CDS
<222> LOCATION: (1)..(609)

-continued

```
<400> SEQUENCE: 20 ggc ata gaa agg gcc aac tca gtc acc tgg aac cct cac aag atg atg      48
Gly Ile Glu Arg Ala Asn Ser Val Thr Trp Asn Pro His Lys Met Met
 1               5                  10                  15 ggc gtg ctg ttg cag tgc tct gcc att ctc gtc aag gaa aag ggt ata      96
Gly Val Leu Leu Gln Cys Ser Ala Ile Leu Val Lys Glu Lys Gly Ile
             20                  25                  30 ctc caa gga tgc aac cag atg tgt gca gga tac ctc ttc cag cca gac     144
Leu Gln Gly Cys Asn Gln Met Cys Ala Gly Tyr Leu Phe Gln Pro Asp
         35                  40                  45 aag cag tat gat gtc tcc tac gac acc ggg gac aag gca att cag tgt     192
Lys Gln Tyr Asp Val Ser Tyr Asp Thr Gly Asp Lys Ala Ile Gln Cys
     50                  55                  60 ggc cgc cac gtg gat atc ttc aag ttc tgg ctg atg tgg aaa gca aag     240
Gly Arg His Val Asp Ile Phe Lys Phe Trp Leu Met Trp Lys Ala Lys
 65                  70                  75                  80 ggc aca gtg gga ttt gaa aac cag atc aac aaa tgc ctg gaa ctg gct     288
Gly Thr Val Gly Phe Glu Asn Gln Ile Asn Lys Cys Leu Glu Leu Ala
                 85                  90                  95 gaa tac ctc tat gcc aag att aaa aac aga gaa gaa ttt gag atg gtt     336
Glu Tyr Leu Tyr Ala Lys Ile Lys Asn Arg Glu Glu Phe Glu Met Val
            100                 105                 110 ttc aat ggc gag cct gag cac aca aac gtc tgt ttt tgg tat att cca     384
Phe Asn Gly Glu Pro Glu His Thr Asn Val Cys Phe Trp Tyr Ile Pro
        115                 120                 125 caa agc ctc agg ggt gtg cca gac agc cct caa cga cgg gaa aag cta     432
Gln Ser Leu Arg Gly Val Pro Asp Ser Pro Gln Arg Arg Glu Lys Leu
    130                 135                 140 cac aag gtg gct cca aaa atc aaa gcc ctg atg atg gag tca ggt acg     480
His Lys Val Ala Pro Lys Ile Lys Ala Leu Met Met Glu Ser Gly Thr
145                 150                 155                 160 acc atg gtt ggc tac cag ccc caa ggg gac aag gcc aac ttc ttc cgg     528
Thr Met Val Gly Tyr Gln Pro Gln Gly Asp Lys Ala Asn Phe Phe Arg
                165                 170                 175 atg gtc atc tcc aac cca gcc gct acc cag tct gac att gac ttc ctc     576
Met Val Ile Ser Asn Pro Ala Ala Thr Gln Ser Asp Ile Asp Phe Leu
            180                 185                 190 att gag gag ata gaa aga ctg ggc cag gat ctg taa                     612
Ile Glu Glu Ile Glu Arg Leu Gly Gln Asp Leu
        195                 200

<210> SEQ ID NO 21
<211> LENGTH: 203
<212> TYPE: PRT
<213> ORGANISM: Unknown Organism
<220> FEATURE:
<223> OTHER INFORMATION: Description of Unknown Organism: C-terminal
      Fragment of Human Brain GAD (HBGAD65)

<400> SEQUENCE: 21

Gly Ile Glu Arg Ala Asn Ser Val Thr Trp Asn Pro His Lys Met Met
 1               5                  10                  15

Gly Val Leu Leu Gln Cys Ser Ala Ile Leu Val Lys Glu Lys Gly Ile
             20                  25                  30

Leu Gln Gly Cys Asn Gln Met Cys Ala Gly Tyr Leu Phe Gln Pro Asp
         35                  40                  45

Lys Gln Tyr Asp Val Ser Tyr Asp Thr Gly Asp Lys Ala Ile Gln Cys
     50                  55                  60

Gly Arg His Val Asp Ile Phe Lys Phe Trp Leu Met Trp Lys Ala Lys
 65                  70                  75                  80
```

```
Gly Thr Val Gly Phe Glu Asn Gln Ile Asn Lys Cys Leu Glu Leu Ala
                85                  90                  95

Glu Tyr Leu Tyr Ala Lys Ile Lys Asn Arg Glu Glu Phe Glu Met Val
            100                 105                 110

Phe Asn Gly Glu Pro Glu His Thr Asn Val Cys Phe Trp Tyr Ile Pro
        115                 120                 125

Gln Ser Leu Arg Gly Val Pro Asp Ser Pro Gln Arg Arg Glu Lys Leu
    130                 135                 140

His Lys Val Ala Pro Lys Ile Lys Ala Leu Met Met Glu Ser Gly Thr
145                 150                 155                 160

Thr Met Val Gly Tyr Gln Pro Gln Gly Asp Lys Ala Asn Phe Phe Arg
                165                 170                 175

Met Val Ile Ser Asn Pro Ala Ala Thr Gln Ser Asp Ile Asp Phe Leu
            180                 185                 190

Ile Glu Glu Ile Glu Arg Leu Gly Gln Asp Leu
        195                 200

<210> SEQ ID NO 22
<211> LENGTH: 1785
<212> TYPE: DNA
<213> ORGANISM: Unknown Organism
<220> FEATURE:
<223> OTHER INFORMATION: Description of Unknown Organism: Full-length
      Nucleotide Sequence of Human Islet GAD (HIGAD-FL)
<220> FEATURE:
<221> NAME/KEY: CDS
<222> LOCATION: (1)..(1782)

<400> SEQUENCE: 22 atg gcg tct tcg acc cca tct tcg tcc gca acc tcc tcg aac gcg gga      48
Met Ala Ser Ser Thr Pro Ser Ser Ser Ala Thr Ser Ser Asn Ala Gly
  1               5                  10                  15 gcg gac ccc aat acc act aac ctg cgc ccc aca acg tac gat acc tgg      96
Ala Asp Pro Asn Thr Thr Asn Leu Arg Pro Thr Thr Tyr Asp Thr Trp
             20                  25                  30 tgc ggc gtg gcc cat gga tgc acc aga aaa ctg ggg ctc aag atc tgc     144
Cys Gly Val Ala His Gly Cys Thr Arg Lys Leu Gly Leu Lys Ile Cys
         35                  40                  45 ggc ttc ttg caa agg acc aac agc ctg gaa gag aag agt cgc ctt gtg     192
Gly Phe Leu Gln Arg Thr Asn Ser Leu Glu Glu Lys Ser Arg Leu Val
     50                  55                  60 agt gcc ttc aag gag agg caa tcc tcc aag aac ctg ctt tcc tgt gaa     240
Ser Ala Phe Lys Glu Arg Gln Ser Ser Lys Asn Leu Leu Ser Cys Glu
 65                  70                  75                  80 aac agc gac cgg gat gcc cgc ttc cgg cgc aca gag act gac ttc tct     288
Asn Ser Asp Arg Asp Ala Arg Phe Arg Arg Thr Glu Thr Asp Phe Ser
                 85                  90                  95 aat ctg ttt gct aga gat ctg ctt ccg gct aag aac ggt gag gag caa     336
Asn Leu Phe Ala Arg Asp Leu Leu Pro Ala Lys Asn Gly Glu Glu Gln
            100                 105                 110 acc gtg caa ttc ctc ctg gaa gtg gtg gac ata ctc ctc aac tat gtc     384
Thr Val Gln Phe Leu Leu Glu Val Val Asp Ile Leu Leu Asn Tyr Val
        115                 120                 125 cgc aag aca ttt gat cgc tcc acc aag gtg ctg gac ttt cat cac cca     432
Arg Lys Thr Phe Asp Arg Ser Thr Lys Val Leu Asp Phe His His Pro
    130                 135                 140 cac cag ttg ctg gaa ggc atg gag ggc ttc aac ttg gag ctc tct gac     480
His Gln Leu Leu Glu Gly Met Glu Gly Phe Asn Leu Glu Leu Ser Asp
145                 150                 155                 160
```

```
cac ccc gag tcc ctg gag cag atc ctg gtc gac tgc aga gac acc ttg      528
His Pro Glu Ser Leu Glu Gln Ile Leu Val Asp Cys Arg Asp Thr Leu
            165                 170                 175 aag tat ggg gtt cgc aca ggt cat cct cga ttt ttc aac cag ctc tcc      576
Lys Tyr Gly Val Arg Thr Gly His Pro Arg Phe Phe Asn Gln Leu Ser
        180                 185                 190 act gga ttg gat att att ggc cta gct gga gaa tgg ctg aca tca acg      624
Thr Gly Leu Asp Ile Ile Gly Leu Ala Gly Glu Trp Leu Thr Ser Thr
    195                 200                 205 gcc aat acc aac atg ttc aca tat gaa att gca cca gtg ttt gtc ctc      672
Ala Asn Thr Asn Met Phe Thr Tyr Glu Ile Ala Pro Val Phe Val Leu
210                 215                 220 atg gaa caa ata aca ctt aag aag atg aga gag ata gtt gga tgg tca      720
Met Glu Gln Ile Thr Leu Lys Lys Met Arg Glu Ile Val Gly Trp Ser
225                 230                 235                 240 agt aaa gat ggt gat ggg ata ttt tct cct ggg ggc gcc ata tcc aac      768
Ser Lys Asp Gly Asp Gly Ile Phe Ser Pro Gly Gly Ala Ile Ser Asn
                245                 250                 255 atg tac agc atc atg gct gct cgc tac aag tac ttc ccg gaa gtt aag      816
Met Tyr Ser Ile Met Ala Ala Arg Tyr Lys Tyr Phe Pro Glu Val Lys
            260                 265                 270 aca aag ggc atg gcg gct gtg cct aaa ctg gtc ctc ttc acc tca gaa      864
Thr Lys Gly Met Ala Ala Val Pro Lys Leu Val Leu Phe Thr Ser Glu
        275                 280                 285 cag agt cac tat tcc ata aag aaa gct ggg gct gca ctt ggc ttt gga      912
Gln Ser His Tyr Ser Ile Lys Lys Ala Gly Ala Ala Leu Gly Phe Gly
    290                 295                 300 act gac aat gtg att ttg ata aag tgc aat gaa agg ggg aaa ata att      960
Thr Asp Asn Val Ile Leu Ile Lys Cys Asn Glu Arg Gly Lys Ile Ile
305                 310                 315                 320 cca gct gat ttt gag gca aaa att ctt gaa gcc aaa cag aag gga tat     1008
Pro Ala Asp Phe Glu Ala Lys Ile Leu Glu Ala Lys Gln Lys Gly Tyr
                325                 330                 335 gtt ccc ttt tat gtc aat gca act gct ggc acg act gtt tat gga gct     1056
Val Pro Phe Tyr Val Asn Ala Thr Ala Gly Thr Thr Val Tyr Gly Ala
            340                 345                 350 ttt gat ccg ata caa gag att gca gat ata tgt gag aaa tat aac ctt     1104
Phe Asp Pro Ile Gln Glu Ile Ala Asp Ile Cys Glu Lys Tyr Asn Leu
        355                 360                 365 tgg ttg cat gtc gat gct gcc tgg gga ggt ggg ctc ctc atg tcc agg     1152
Trp Leu His Val Asp Ala Ala Trp Gly Gly Gly Leu Leu Met Ser Arg
    370                 375                 380 aag cac cgc cat aaa ctc aac ggc ata gaa agg gcc aac tca gtc acc     1200
Lys His Arg His Lys Leu Asn Gly Ile Glu Arg Ala Asn Ser Val Thr
385                 390                 395                 400 tgg aac cct cac aag atg atg ggc gtg ctg ttg cag tgc tct gcc att     1248
Trp Asn Pro His Lys Met Met Gly Val Leu Leu Gln Cys Ser Ala Ile
                405                 410                 415 ctc gtc aag gaa aag ggt ata ctc caa gga tgc aac cag atg tgt gca     1296
Leu Val Lys Glu Lys Gly Ile Leu Gln Gly Cys Asn Gln Met Cys Ala
            420                 425                 430 gga tac ctc ttc cag cca gac aag cag tat gat gtc tcc tac gac acc     1344
Gly Tyr Leu Phe Gln Pro Asp Lys Gln Tyr Asp Val Ser Tyr Asp Thr
        435                 440                 445 ggg gac aag gca att cag tgt ggc cgc cac gtg gat atc ttc aag ttc     1392
Gly Asp Lys Ala Ile Gln Cys Gly Arg His Val Asp Ile Phe Lys Phe
    450                 455                 460 tgg ctg atg tgg aaa gca aag ggc aca gtg gga ttt gaa aac cag atc     1440
Trp Leu Met Trp Lys Ala Lys Gly Thr Val Gly Phe Glu Asn Gln Ile
465                 470                 475                 480
```

```
aac aaa tgc ctg gaa ctg gct gaa tac ctc tat gcc aag att aaa aac    1488
Asn Lys Cys Leu Glu Leu Ala Glu Tyr Leu Tyr Ala Lys Ile Lys Asn
                485                 490                 495 aga gaa gaa ttt gag atg gtt ttc aat ggc gag cct gag cac aca aac    1536
Arg Glu Glu Phe Glu Met Val Phe Asn Gly Glu Pro Glu His Thr Asn
                500                 505                 510 gtc tgt ttt tgg tat att cca caa agc ctc agg ggt gtg cca gac agc    1584
Val Cys Phe Trp Tyr Ile Pro Gln Ser Leu Arg Gly Val Pro Asp Ser
                515                 520                 525 cct caa cga cgg gaa aag cta cac aag gtg gct cca aaa atc aaa gcc    1632
Pro Gln Arg Arg Glu Lys Leu His Lys Val Ala Pro Lys Ile Lys Ala
        530                 535                 540 ctg atg atg gag tca ggt acg acc atg gtt ggc tac cag ccc caa ggg    1680
Leu Met Met Glu Ser Gly Thr Thr Met Val Gly Tyr Gln Pro Gln Gly
545                 550                 555                 560 gac aag gcc aac ttc ttc cgg atg gtc atc tcc aac cca gcc gct acc    1728
Asp Lys Ala Asn Phe Phe Arg Met Val Ile Ser Asn Pro Ala Ala Thr
                565                 570                 575 cag tct gac att gac ttc ctc att gag gag ata gaa aga ctg ggc cag    1776
Gln Ser Asp Ile Asp Phe Leu Ile Glu Glu Ile Glu Arg Leu Gly Gln
                580                 585                 590 gat ctg taa                                                         1785
Asp Leu <210> SEQ ID NO 23
<211> LENGTH: 594
<212> TYPE: PRT
<213> ORGANISM: Unknown Organism
<220> FEATURE:
<223> OTHER INFORMATION: Description of Unknown Organism: Human Islet
      GAD (HIGAD-FL)

<400> SEQUENCE: 23

Met Ala Ser Ser Thr Pro Ser Ser Ser Ala Thr Ser Ser Asn Ala Gly
  1               5                  10                  15

Ala Asp Pro Asn Thr Thr Asn Leu Arg Pro Thr Thr Tyr Asp Thr Trp
                 20                  25                  30

Cys Gly Val Ala His Gly Cys Thr Arg Lys Leu Gly Leu Lys Ile Cys
             35                  40                  45

Gly Phe Leu Gln Arg Thr Asn Ser Leu Glu Glu Lys Ser Arg Leu Val
         50                  55                  60

Ser Ala Phe Lys Glu Arg Gln Ser Ser Lys Asn Leu Leu Ser Cys Glu
 65                  70                  75                  80

Asn Ser Asp Arg Asp Ala Arg Phe Arg Arg Thr Glu Thr Asp Phe Ser
                 85                  90                  95

Asn Leu Phe Ala Arg Asp Leu Leu Pro Ala Lys Asn Gly Glu Glu Gln
                100                 105                 110

Thr Val Gln Phe Leu Leu Glu Val Val Asp Ile Leu Leu Asn Tyr Val
            115                 120                 125

Arg Lys Thr Phe Asp Arg Ser Thr Lys Val Leu Asp Phe His His Pro
        130                 135                 140

His Gln Leu Leu Glu Gly Met Glu Gly Phe Asn Leu Glu Leu Ser Asp
145                 150                 155                 160

His Pro Glu Ser Leu Glu Gln Ile Leu Val Asp Cys Arg Asp Thr Leu
                165                 170                 175

Lys Tyr Gly Val Arg Thr Gly His Pro Arg Phe Phe Asn Gln Leu Ser
            180                 185                 190
```

```
Thr Gly Leu Asp Ile Ile Gly Leu Ala Gly Glu Trp Leu Thr Ser Thr
            195                 200                 205

Ala Asn Thr Asn Met Phe Thr Tyr Glu Ile Ala Pro Val Phe Val Leu
    210                 215                 220

Met Glu Gln Ile Thr Leu Lys Lys Met Arg Glu Ile Val Gly Trp Ser
225                 230                 235                 240

Ser Lys Asp Gly Asp Gly Ile Phe Ser Pro Gly Gly Ala Ile Ser Asn
                245                 250                 255

Met Tyr Ser Ile Met Ala Ala Arg Tyr Lys Tyr Phe Pro Glu Val Lys
            260                 265                 270

Thr Lys Gly Met Ala Ala Val Pro Lys Leu Val Leu Phe Thr Ser Glu
        275                 280                 285

Gln Ser His Tyr Ser Ile Lys Lys Ala Gly Ala Ala Leu Gly Phe Gly
    290                 295                 300

Thr Asp Asn Val Ile Leu Ile Lys Cys Asn Glu Arg Gly Lys Ile Ile
305                 310                 315                 320

Pro Ala Asp Phe Glu Ala Lys Ile Leu Glu Ala Lys Gln Lys Gly Tyr
                325                 330                 335

Val Pro Phe Tyr Val Asn Ala Thr Ala Gly Thr Thr Val Tyr Gly Ala
            340                 345                 350

Phe Asp Pro Ile Gln Glu Ile Ala Asp Ile Cys Glu Lys Tyr Asn Leu
        355                 360                 365

Trp Leu His Val Asp Ala Ala Trp Gly Gly Gly Leu Leu Met Ser Arg
370                 375                 380

Lys His Arg His Lys Leu Asn Gly Ile Glu Arg Ala Asn Ser Val Thr
385                 390                 395                 400

Trp Asn Pro His Lys Met Met Gly Val Leu Leu Gln Cys Ser Ala Ile
                405                 410                 415

Leu Val Lys Glu Lys Gly Ile Leu Gln Gly Cys Asn Gln Met Cys Ala
            420                 425                 430

Gly Tyr Leu Phe Gln Pro Asp Lys Gln Tyr Asp Val Ser Tyr Asp Thr
        435                 440                 445

Gly Asp Lys Ala Ile Gln Cys Gly Arg His Val Asp Ile Phe Lys Phe
    450                 455                 460

Trp Leu Met Trp Lys Ala Lys Gly Thr Val Gly Phe Glu Asn Gln Ile
465                 470                 475                 480

Asn Lys Cys Leu Glu Leu Ala Glu Tyr Leu Tyr Ala Lys Ile Lys Asn
                485                 490                 495

Arg Glu Glu Phe Glu Met Val Phe Asn Gly Glu Pro Glu His Thr Asn
            500                 505                 510

Val Cys Phe Trp Tyr Ile Pro Gln Ser Leu Arg Gly Val Pro Asp Ser
        515                 520                 525

Pro Gln Arg Arg Glu Lys Leu His Lys Val Ala Pro Lys Ile Lys Ala
    530                 535                 540

Leu Met Met Glu Ser Gly Thr Thr Met Val Gly Tyr Gln Pro Gln Gly
545                 550                 555                 560

Asp Lys Ala Asn Phe Phe Arg Met Val Ile Ser Asn Pro Ala Ala Thr
                565                 570                 575

Gln Ser Asp Ile Asp Phe Leu Ile Glu Glu Ile Glu Arg Leu Gly Gln
            580                 585                 590

Asp Leu

<210> SEQ ID NO 24
```

```
<211> LENGTH: 29
<212> TYPE: DNA
<213> ORGANISM: Unknown Organism
<220> FEATURE:
<223> OTHER INFORMATION: Description of Unknown Organism:
      Oligonucleotide Primer (RGAD1)

<400> SEQUENCE: 24
attggatcca ccgagctgat ggcgtcttc                                    29

<210> SEQ ID NO 25
<211> LENGTH: 27
<212> TYPE: DNA
<213> ORGANISM: Unknown Organism
<220> FEATURE:
<223> OTHER INFORMATION: Description of Unknown Organism:
      Oligonucleotide Primer (RGAD2)

<400> SEQUENCE: 25
ccgaattcgc cattcgccag ctaaacc                                      27

<210> SEQ ID NO 26
<211> LENGTH: 28
<212> TYPE: DNA
<213> ORGANISM: Unknown Organism
<220> FEATURE:
<223> OTHER INFORMATION: Description of Unknown Organism:
      Oligonucleotide Primer (RGAD3)

<400> SEQUENCE: 26
attggatccg gtttagctgg cgaatggc                                     28

<210> SEQ ID NO 27
<211> LENGTH: 27
<212> TYPE: DNA
<213> ORGANISM: Unknown Organism
<220> FEATURE:
<223> OTHER INFORMATION: Description of Unknown Organism:
      Oligonucleotide Primer (RGAD4)

<400> SEQUENCE: 27
ccgaattctg tgagggttcc aggtgac                                      27

<210> SEQ ID NO 28
<211> LENGTH: 28
<212> TYPE: DNA
<213> ORGANISM: Unknown Organism
<220> FEATURE:
<223> OTHER INFORMATION: Description of Unknown Organism:
      Oligonucleotide Primer (RGAD5)

<400> SEQUENCE: 28
attggatccg tcacctggaa ccctcaca                                     28

<210> SEQ ID NO 29
<211> LENGTH: 26
<212> TYPE: DNA
<213> ORGANISM: Unknown Organism
<220> FEATURE:
<223> OTHER INFORMATION: Description of Unknown Organism:
      Oligonucleotide Primer (RGAD6)

<400> SEQUENCE: 29
ccgaattcat tacagatcct ggccca                                       26

<210> SEQ ID NO 30
<211> LENGTH: 29
```

```
<212> TYPE: DNA
<213> ORGANISM: Unknown Organism
<220> FEATURE:
<223> OTHER INFORMATION: Description of Unknown Organism:
      Oligonucleotide (GAD1)

<400> SEQUENCE: 30
actgccaata ccaatatgtt cacatatga                                      29

<210> SEQ ID NO 31
<211> LENGTH: 20
<212> TYPE: DNA
<213> ORGANISM: Unknown Organism
<220> FEATURE:
<223> OTHER INFORMATION: Description of Unknown Organism:
      Oligonucleotide (GAD5)

<400> SEQUENCE: 31
cccataaact catgttcttg                                                20

<210> SEQ ID NO 32
<211> LENGTH: 20
<212> TYPE: DNA
<213> ORGANISM: Unknown Organism
<220> FEATURE:
<223> OTHER INFORMATION: Description of Unknown Organism:
      Oligonucleotide (GAD7)

<400> SEQUENCE: 32
ggagaaaata tcccatcacc                                                20

<210> SEQ ID NO 33
<211> LENGTH: 28
<212> TYPE: DNA
<213> ORGANISM: Unknown Organism
<220> FEATURE:
<223> OTHER INFORMATION: Description of Unknown Organism:
      Oligonucleotide (RGAD4)

<400> SEQUENCE: 33
ccgaattctg tagagggttc caggtgac                                       28

<210> SEQ ID NO 34
<211> LENGTH: 26
<212> TYPE: DNA
<213> ORGANISM: Unknown Organism
<220> FEATURE:
<223> OTHER INFORMATION: Description of Unknown Organism:
      Oligonucleotide (GAD6)

<400> SEQUENCE: 34
attggatccg gcatagaaag ggccaa                                         26
```